(12) United States Patent
Washizu et al.

(10) Patent No.: US 7,497,107 B2
(45) Date of Patent: Mar. 3, 2009

(54) GAS SENSING MATERIAL AND GAS INSPECTING METHOD

(75) Inventors: Shintaro Washizu, Tokyo (JP); Munehisa Fujita, Kanagawa (JP)

(73) Assignee: Fuji Photo Film Co., Ltd., Minami-Ashigara-shi (JP)

( * ) Notice: Subject to any disclaimer, the term of this patent is extended or adjusted under 35 U.S.C. 154(b) by 0 days.

(21) Appl. No.: 11/033,450

(22) Filed: Jan. 12, 2005

(65) Prior Publication Data
US 2005/0207944 A1 Sep. 22, 2005

(30) Foreign Application Priority Data
Jan. 14, 2004 (JP) .............. 2004-006962
Dec. 8, 2004 (JP) .............. 2004-356064

(51) Int. Cl.
*G01N 7/00* (2006.01)
*G03C 1/00* (2006.01)

(52) U.S. Cl. .............. 73/23.2; 430/618

(58) Field of Classification Search .............. 430/618; 73/23.2
See application file for complete search history.

(56) References Cited

U.S. PATENT DOCUMENTS

| | | | | |
|---|---|---|---|---|
| 3,839,049 A | * | 10/1974 | Simons | ............ 430/619 |
| 4,902,308 A | * | 2/1990 | Mallouk et al. | ............ 95/50 |
| 5,705,324 A | | 1/1998 | Murray | |
| 6,217,827 B1 | | 4/2001 | Zhang et al. | |
| 6,528,244 B1 | * | 3/2003 | Katoh et al. | ............ 430/619 |

FOREIGN PATENT DOCUMENTS

| | | |
|---|---|---|
| EP | 0 803 764 | 10/1997 |
| JP | 2003131337 | 5/2003 |
| WO | 02/066971 | 8/2002 |

OTHER PUBLICATIONS

European Patent Office Communication for corresponding European search report on the European Patent Application No. 05000491 dated May 3, 2005.
Koyama, K., et al. "Observation of Impurity Hydrogen evolved from Aluminum and Titanium Alloys during Deformation by means of Hydrogen Microprint Technique;" *Journal of Japan Institute of Metals*, vol. 62, No. 9, pp. 790-795 (1998) with partial English translation.
Nagao, A., et al. "Detection and visualization of hydrogen in aluminum;" *Journal of Japan institute of Light Metals*, vol. 49, No. 2, pp. 89-96 (1996) with partial English translation.

* cited by examiner

*Primary Examiner*—Michael Cygan
(74) *Attorney, Agent, or Firm*—Kratz, Quintos & Hanson, LLP

(57) ABSTRACT

A gas sensing material includes a nonphotosensitive organic silver salt. A gas inspecting method includes adhering a gas sensing material to a surface of an inspection object, wherein the gas sensing material includes a nonphotosensitive organic silver salt; and heat developing the gas sensing material.

26 Claims, 2 Drawing Sheets

GAS SENSING MATERIAL AND GAS INSPECTING METHOD

BACKGROUND OF THE INVENTION

1. Field of the Invention

The present invention relates to a gas sensing material for sensing a local gas leaked or ejected from an inspection object. The present invention also relates to a gas inspecting method which uses the gas sensing material, is easy to carry out and is capable of carrying out sensing rapidly with high accuracy.

2. Description of the Related Art

Recently, hydrogen gas is attracting more and more attention. One reason for that is an energy problem, therefore, use of the hydrogen gas which is environmentally clean is taken into account in various fields. Examples of the application of the hydrogen gas include an electric vehicle having a fuel cell as its energy source, and a hydrogen vehicle with hydrogen fuel stored in a hydrogen storage alloy tank, and the like. Moreover, the following hydrogen energy society is expected: an energy obtained by any of a hydraulic power generation, a wind power generation, a photovoltaic power generation, an atomic power generation and the like is once converted into a hydrogen in a hydrogen manufacturing plant, then the hydrogen is stored in a hydrogen storage tank, for energy distribution to various applications of social life such as family fuel, traffic-and-transportation fuel and the like.

Another problem is structural material's brittleness caused by hydrogen. Recently, it has been obvious that the structural material becomes brittle and deteriorated due to water content in the environment or hydrogen caused by the water content. Clarifying the hydrogen's function which is deemed to be the main cause of the above structural material's brittleness may lead to solution of a long-year problem (environmental brittleness) in the field of material technology, giving a strong assistance to material problems indispensable for social infrastructure arrangement-maintenance and various big projects. Moreover, clarifying the hydrogen's function is expected to bring about a pervasive effect on the environmental countermeasure and a new technology in the field of electronics. However, the hydrogen in the structural material has an ultrafine amount of ppm digit and is likely to be mobile, therefore it is difficult to catch reality of the hydrogen. Moreover, a method of observing microscopic feature of destruction is not established. With the above, clarification of the environmental brittleness and its drastic countermeasure guideline are not making so much a progress as expected.

In terms of the above two social changes, development of a new sensing unit for sensing the hydrogen gas is required, especially, observation of microscopic hydrogen state involved by the structural material's brittleness caused by hydrogen, specifying hydrogen leak part in a hydrogen bomb, and an inspecting-analyzing method of carrying out the above easily, rapidly, highly accurately and quantitatively.

In the above state, Hydrogen MicroPrint Technique (hereinafter referred to as "HMPT method" as the case may be) which is a visualization technology of the hydrogen state in the structural material is attracting attention (for example, refer to "The Japan Institute of Metals, Vol. 62, No. 9, (1998), pp. 790-795" and "Light metal, No. 49, second issue (1999), pp. 89-96" and the like). The above "HMPT method" is a method of analyzing mobile behavior of the hydrogen, by using a direct reducing operation of an atomic hydrogen reaching the surface the structural material from inside of the structural material.

FIG. 1A shows a principle of the above hydrogen microprint technique (HMPT method), in which a photographic emulsion film 5 is so applied as to coat a surface of a hydrogen bomb 10 which is an inspection object. In the above state, when the atomic hydrogen in the hydrogen bomb 10 is leaked or ejected to the surface of the hydrogen bomb 10 for some reasons, a silver bromide (AgBr) 1 (which is present in a place to which the hydrogen is ejected) in the photographic emulsion layer 5 may be reduced to a silver atom (Ag) 3, as expressed by the following reaction formula 1 (refer to FIG. 1B). The above reduction of the silver bromide (AgBr) 1 to the silver atom (Ag) 3 is attributable to a strong reducing operation of the atomic hydrogen. Then, carrying out development and fixing treatment of the photographic emulsion film 5 in combination with the inspection object 10 may grow the thus caused silver atom (Ag) 3 to a silver particle (Ag) 3' which can be observed by a microscope. On the other hand, an unreacted silver bromide (AgBr) 1 may be dissolved in a fixing liquid in the fixing, thereby, finally, the silver particle (Ag) 3' alone may remain on the surface of the inspection object (refer to FIG. 1C). The hydrogen's mobile behavior can be checked by observing, with an optical microscope and an SEM (scanning electronic microscope), the thus remaining silver particle (Ag) 3'.

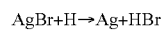 <Reaction formula 1>

The above HMPT method is epochal for its capability of sensing the local leak and local ejection of the hydrogen gas of the structural material, which sensing was conventional difficult. However, the HMPT method using the photographic emulsion may require an expert skill for operation in a dark room. Moreover, the HMPT method in need of developing treatment of the photographic emulsion may require equipment (development to fixing) and complicated operations. Moreover, in the HMPT method, the photographic emulsion film cannot be applied to the inspection object with high accuracy and the operation is complicated, therefore light-preventing property to the photographic emulsion is insufficient, failing to obtain sufficient accuracy.

Summarizing the above, the development of the gas inspecting method and the gas sensing material for the method is strongly demanded, which method enables an easy operation in a bright room and is capable of sensing rapidly and with high accuracy the local gas leaked or ejected from the inspection object.

OBJECTS AND ADVANTAGES

It is therefore an object of the present invention to provide a gas inspecting method and a gas sensing material used for the method, which method enables an easy operation in a bright room and is capable of sensing rapidly and with high accuracy a local gas leaked or ejected from an inspection object.

SUMMARY OF THE INVENTION

According to a first aspect of the present invention, there is provided a gas sensing material which comprises a nonphotosensitive organic silver salt.

According to a second aspect of the present invention, there is provided a gas sensing material which comprises a support; and a gas sensing layer which comprises a nonphotosensitive organic silver salt and is located on the support.

With the gas sensing material according to the first aspect and the second aspect, after being reduced by hydrogen gas or being sulphurized with a sulfur-contained gas, and thereafter preferably being heat developed under the presence of a heat developer, the nonphotosensitive organic silver salt may form a monochrome image by a silver image. Then, the silver image forming position can specify the hydrogen gas leak part, and the silver image density or the silver image forming amount can quantify the hydrogen gas quantity.

The gas sensing material according to the second aspect, especially having an adhesive layer, can be sealably attached to the inspection object via the adhesive layer, decreasing the inspection time, and easing the inspecting operation thereby eliminating the need for an expert skill. Moreover, the application amount of the gas sensing material becoming constant can improve accuracy and reproducibility of the inspection. Moreover, measuring developing quantity of the above organic silver salt can accomplish a quantitative measurement.

The gas inspecting method of the present invention comprises adhering and heat developing. In the adhering, the gas sensing material according to the first aspect and the second aspect of the present invention is adhered to a surface of the inspection object, to be reacted with a gas leaked or ejected from the inspection object. In the heat developing, the gas sensing material is to be heat developed, for amplification and visualization.

With the gas inspecting method of the present invention, the experimental results may have high repeatability and reproducibility even in a bright room and have high accuracy, with the experiment carried out in a short time. Moreover, being free from the need of complicated developing treatment, the gas inspecting method of the present invention does not need the expert skill in the experiment, making it possible to carry out all processes in the bright room. In addition, no material is removed from the gas sensing material, thus causing no waste liquid or scraps, which is excellent in environmental friendliness.

BRIEF DESCRIPTION OF THE DRAWING

FIG. 1A shows a photographic emulsion film which is applied onto a surface of a hydrogen bomb which is an inspection object. FIG. 1B shows that an atomic hydrogen which is leaked or ejected to the surface of the hydrogen bomb reduces a silver bromide (in the photographic emulsion film) to a silver atom. FIG. 1C shows a state where the photographic emulsion film is developed and fixed.

FIG. 2A shows the gas sensing material which is applied onto a surface of a hydrogen bomb which is an inspection object. FIG. 2B shows that an atomic hydrogen which is leaked or ejected to the surface of the hydrogen bomb reduces a nonphotosensitive organic silver salt (in the gas sensing material). FIG. 2C shows a state where the gas sensing material is developed.

DESCRIPTION OF THE PREFERRED EMBODIMENTS (Gas Sensing Material)

The gas sensing material according to the first embodiment of the present invention contains at least a nonphotosensitive organic silver salt, further contains a binder, heat a developer, and moreover contains when necessary, other component(s).

The gas sensing material according to the second embodiment of the present invention contains at least a support and a gas sensing layer, further contains an adhesive layer, and moreover contains when necessary, other layer(s). The above gas sensing layer contains at least a nonphotosensitive organic silver salt, further contains a binder and a heat developer, and moreover contains when necessary other component(s).

Preferably, the above gas sensing material is adhered to an inspection object, to thereby sense a gas leaked or ejected from a surface of the inspection object.

Examples of the above gas include at least one of hydrogen gas and sulfur-contained gas. Examples of the above sulfur-contained gas include $H_2S$, $SO_2$, and the like.

Figure 1A:
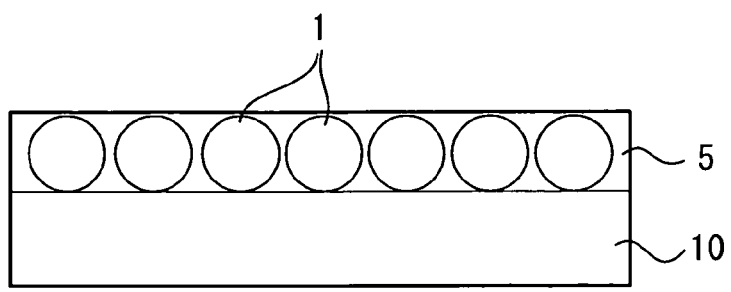
FIG. 1A, FIG. 1B and FIG. 1C are schematics for explaining a principle of a conventional hydrogen microprint technique (HMPT method).
Figure 1B:
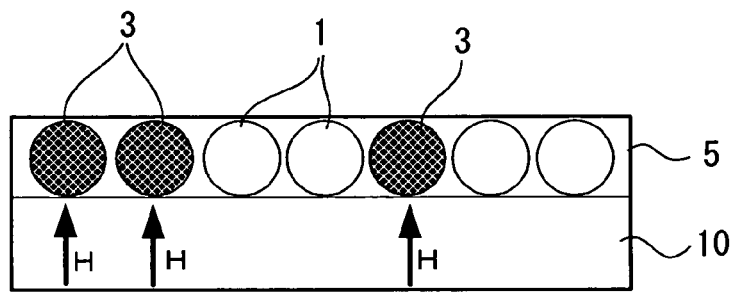
Figure 1C:
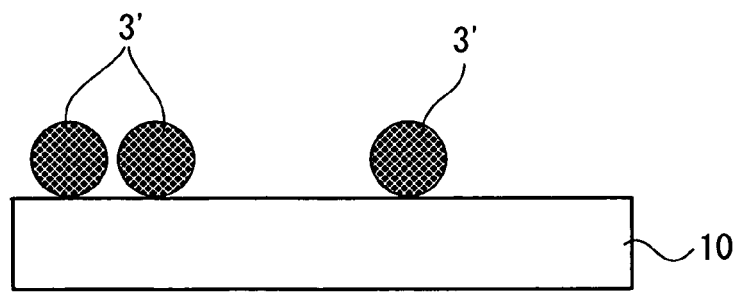
Figure 2A:
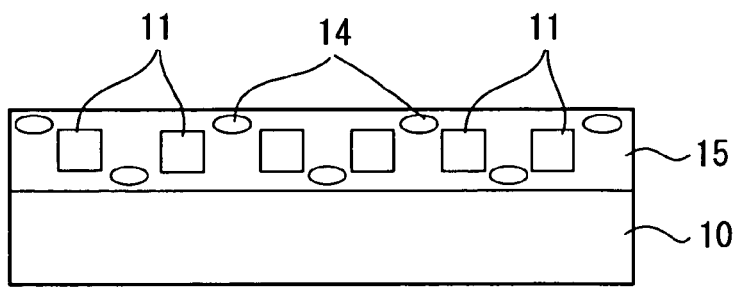
FIG. 2A, FIG. 2B and FIG. 2C are schematics for explaining a principle of a gas inspecting method using a gas sensing material of the present invention.

FIG. 2A shows a principle of sensing the gas, by using the gas sensing material of the present invention. In FIG. 2A, a surface of a hydrogen bomb 10 which is an inspection object is coated with a gas sensing material 15. In the gas sensing material 15, a nonphotosensitive organic silver salt 11 and a heat developer 14 are contained.

Figure 2B:
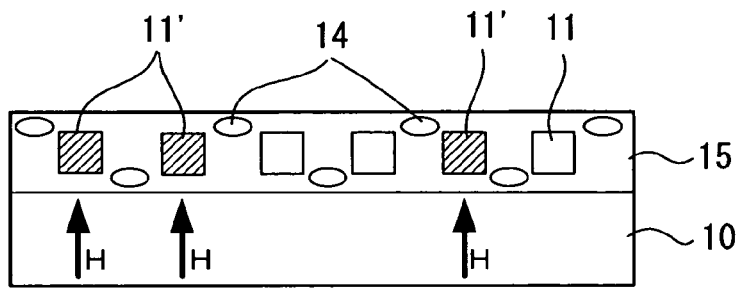
Figure 2C:
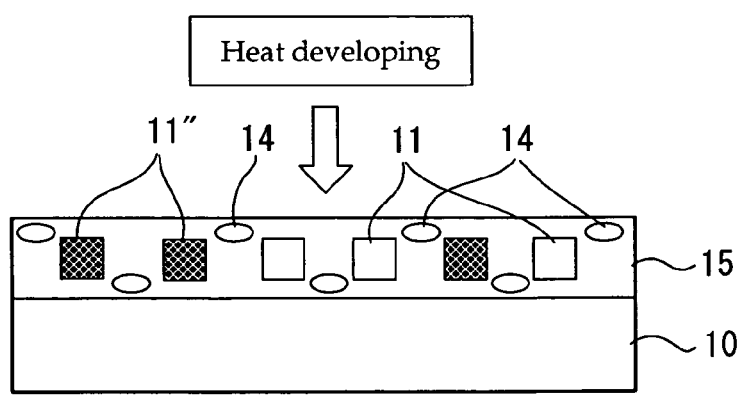

In the above state, when an atomic hydrogen in the hydrogen bomb 10 is leaked or ejected to the surface of the hydrogen bomb 10 for some reasons, the nonphotosensitive organic silver salt 11 (in the gas sensing material) which is present in a place to which the hydrogen is ejected may be reduced (refer to FIG. 2B) to a reduced nonphotosensitive organic silver salt 11'. The above reduction of the nonphotosensitive organic silver salt 11 to the reduced nonphotosensitive organic silver salt 11' is attributable to a strong reducing operation of the atomic hydrogen. Then, subjecting the gas sensing material 15 to a heat developing treatment may grow the thus reduced nonphotosensitive organic silver salt 11' to a silver particle 11" that can be observed with a microscope, thereby forming a silver image (refer to FIG. 2C). Then, cooling down to an ordinary temperature may stop the reaction. Observing the thus obtained silver particle 11" with an optical microscope or an SEM (scanning electronic microscope) can check the hydrogen's mobile behavior.

In the above method, a special fixing operation is not necessary after the heat developing operation. Moreover, no material is removed from the gas sensing material 15, thus causing no waste liquid and scrap. Moreover, all operations can be carried out in a bright room, making the operation easy.

Nonphotosensitive Organic Silver Salt

The above nonphotosensitive organic silver salt according to a first embodiment is contained in the above gas sensing material, while according to the second embodiment is contained the above gas sensing layer.

The above nonphotosensitive organic silver salt is stable to light. After being reduced by hydrogen gas or being sulphurized with a sulfur-contained gas, however, the nonphotosensitive organic silver salt may form a silver image when heated at 80° C. or more preferably under the presence of the heat developer. The above organic silver salt may be an arbitrary organic material silver containing a source which is capable of reducing a silver ion.

Examples of the above nonphotosensitive organic silver salt include those described in Japanese Patent Application Laid-Open (JP-A) No. 10-62899 (paragraph No. 0048 to paragraph No. 0049), EP0803764A1 (line 24 at page 18 to line 37 at page 19), EP0962812A1, JP-A No. 11-349591, JP-A No. 2000-7683, JP-A No. 2000-72711, and the like.

As the silver salt of the above nonphotosensitive organic acid, a silver salt of a long-chain aliphatic carboxylic acid is preferable. The long-chain aliphatic carboxylic acid preferably has 10 to 30 carbon atoms, and more preferably 15 to 28, examples thereof including, behenic acid silver, arachidic acid silver, stearic acid silver, oleic acid silver, lauric acid silver, caproic acid silver, myristic acid silver, palmitic acid silver, a mixture thereof, and the like. Among the above, the behenic acid silver is especially preferable. Content of the behenic acid silver is preferably 50% by mol to 100% by mol, and more preferably 75% by mol to 98% by mol.

Shape of the above organic silver salt is not specifically limited, and therefore may be properly selected according to the object, for example, needle-shape, rod-shape, flat plate-shape, scale-shape, and the like. Among the above, the scale-shaped organic silver salt is preferable. In this specification, the above scale-shaped organic silver salt is to be defined in the following manner. When the above organic silver salt is observed with an electronic microscope, the shape of the organic silver salt particle is to be approximated to a rectangular parallelopiped which has a side AA, a side BB, and a side CC in the order of length (the side CC and the side BB may be the same), the shorter numerical values AA and BB are to be used for the calculation of the following equation: X=BB/AA.

In the above manner, the X is to be calculated for about 200 particles, and an X (average) meeting: X (average)≧1.5 is defined as the scale-shape. The X is preferred to be 30≧X (average)≧1.5, and more preferably 20≧X (average)≧2.0. Herein, the needle-shape meets 1≦X (average)<1.5.

In the above scale-shaped particle, the side AA is deemed as thickness of a flat plate-shaped particle having a main flat face which is formed by the side BB and the side CC. The side AA has a preferable average of 0.01 μm to 0.23 μm, and more preferably 0.1 μm to 0.20 μm. The ratio CC/BB has a preferable average of 1 to 6, more preferably 1.05 to 4, still more preferably 1.1 to 3, and especially preferably 1.1 to 2.

In terms of a particle size distribution, the above organic silver salt is preferred to have a single dispersion. With the single dispersion, standard deviations of a short axis's length and a long axis's length divided respectively by the short axis and the long axis have a preferable percentage of 100% or less, more preferably 80% or less, and especially preferably 50% or less.

Herein, the shape of the above organic silver salt can be measured with a transmissive electronic microscopic image of an organic silver salt dispersed matter. Otherwise, the single dispersive property can be measured by obtaining the standard deviation of volume weight average diameter of the organic silver salt, where the value divided by the volume weight average diameter has a preferable percentage (coefficient of variation) of 100% or less, more preferably 80% or less, and especially preferably 50% or less. The shape of the organic silver salt can be measured, for example, by the following method: i) irradiating a laser beam to an organic silver salt which is dispersed in a liquid, ii) obtaining autocorrelation function relative to time change of the scattered light's fluctuation to thereby obtain particle size (volume weight average diameter).

A manufacturing method and a dispersing method of the above nonphotosensitive organic silver salt may be those known in the art. Examples thereof include JP-A No. 10-62899 described above, EP0803764A1 described above, EP0962812A1 described above, JP-A No. 11-349591 described above, JP-A No. 2000-7683 described above, JP-A No. 2000-72711 described above, JP-A No. 2001-163889, JP-A No. 2001-163890, JP-A No. 2001-163827, JP-A No. 2001-33907, JP-A No. 2001-188313, JP-A No. 2001-83652, JP-A No. 2002-6442, JP-A No. 2002-31870, and the like.

Content of the above nonphotosensitive organic silver salt is preferably, as a silver amount, 0.1 g/m$^2$ to 5 g/m$^2$, more preferably 1 g/m$^2$ to 3 g/m$^2$, and especially preferably 1.2 g/m$^2$ to 2.5 g/m$^2$.

The content of the above nonphotosensitive organic silver salt, as the silver amount, less than 0.1 g/m$^2$ may not bring about a sufficient transmission OD (optical density), failing to secure quantitative property and dynamic range, while more than 5 g/m$^2$ may bring about transmission OD 4.0 or more, which is practically a saturation density, in other words, adding more than this may just lead to cost increase.

Of the present invention, the gas sensing material according to the first embodiment and the gas sensing layer may contain, in addition to the above nonphotosensitive organic silver, a binder and a heat developer, and moreover may contain when necessary other components.

Binder

The above binder is not specifically limited, and therefore may be selected from a polymer ordinarily used for the gas sensing material, is preferably transparent or semitransparent, and is generally colorless. Specific examples thereof include a natural resin, a natural polymer, a natural copolymer, a synthetic resin, a synthetic polymer, a synthetic copolymer, and the like.

Specific examples of the above binder include gelatins, rubbers, poly(vinyl alcohol)s, hydroxy ethyl celluloses, cellulose acetates, cellulose acetate butyrates, poly(vinyl pyrrolidone)s, casein, starch, poly(acrylic acid)s, poly(methyl methacrylic acid)s, poly(vinyl chloride)s, poly(methacrylic acid)s, styrene-maleic acid anhydride copolymers, styrene-acrylonitrile copolymers, styrene-butadiene copolymers, poly(vinyl acetal)s (for example, poly(vinyl formal) and poly (vinyl butyral)), poly(ester)s, poly(urethane)s, phenoxy resin, poly(vinylidene chloride)s, poly(epoxide)s, poly(carbonate) s, poly(vinyl acetate)s, poly(oleofine)s, cellulose esters, poly (amide)s, and the like.

The above binder has a preferable glass transition temperature (Tg) 0° C. to 80° C. (hereinafter, referred to as "high Tg binder" as the case may be), more preferably 10° C. to 70° C., and especially preferably 15° C. to 60° C.

Herein, the above glass transition temperature (Tg) may be calculated from the following mathematical expression.

$1/Tg = \Sigma(Xi/Tgi)$  <Mathematical expression 2>

In the above mathematical expression 2, a polymer is a copolymerization of n pieces of monomer components (i=1 to n). Xi is a weight ratio ($\Sigma Xi=1$) an "i"th monomer, Tgi is a glass transition temperature (absolute temperature) of a single polymer of the "i"th monomer. Hereinabove, $\Sigma$ is a summation from i=1 to n.

Herein, the single polymer glass transition temperature (Tgi) of each of the monomers is cited from the one described in Polymer Handbook (3rd Edition) (written by J. Brandrup, E. H. Immergut (Wiley-Interscience, 1989)).

The polymer becoming the above binder may be used alone, or when necessary in combination of two or more. Moreover, a binder having the glass transition temperature 20° C. or more and a binder having the glass transition temperature 20° C. less than may be combined. When two or more the polymers having different Tgs are to be blended, the weight average of the polymer glass transition temperature Tg is preferred to be within the above range.

The above high Tg polymer fine dispersed matter can be obtained through an ordinary polymerization reaction such as emulsification polymerization, dispersion polymerization, suspension polymerization, and the like. In this case, however, with the fact that most of the application (coating) of the photosensitive material uses water as medium, and that the non water-soluble material such as the copolymer is used in a form of a water dispersed matter, the emulsification polymerization and the dispersion polymerization are preferable from the viewpoint of preparation of application liquid, especially preferably a synthesis by the emulsification polymerization. When the latex is used, ordinarily, the fine particle has a preferable particle diameter 300 nm or less, more preferably 200 nm or less, and especially preferably 150 nm or less.

The above emulsification polymerization method is, for example, carried out in the following manner: i) prepare a dispersion medium which is a mixture solvent of water and an organic solvent (for example, methanol, ethanol, acetone, and the like) capable of being mixed with the water, ii) use a monomer mixture 5% by mass to 40% by mass to the dispersion medium, and use for the monomer A) a polymerization starting agent 0.05% by mass to 5% by mass and B) an emulsifier 0.1% by mass to 20% by mass, iii) carry out polymerization under a stirring state at about 30° to about 100°, preferably at 60° C. to 90° C. for 3 hours to 8 hours. Conditions of the dispersion medium, the monomer's density, the starting agent's amount, the emulsifier's amount, the reaction temperature, time, monomer adding method and the like may be properly determined, in view of the monomer's type, the particle's target particle diameter, and the like.

Examples of the starting agents used for the above emulsification polymerization include i) inorganic peroxides such as potassium persulfate, sodium persulfate, ammonium persulfate and the like, ii) azonitril compound such as sodium salt of azobis cyano valerianic acid, and the like, iii) azoamidine compound such as 2,2'-azobis (2-amidino propane) dihydrochloride, and the like, iv) ring-shaped azoamidine compound such as 2,2'-azobis (2-(5-methyl-2-imidazoline-2-yl) propane) hydrochloride, and the like, v) azo amide compound such as 2,2'-azobis (2-methyl-N-(1,1'-bis(hydroxy methyl)-2-hydroxy ethyl) propione amide), and the like. Among the above, potassium persulfate, sodium persulfate, and ammonium persulfate are especially preferable.

Examples of the above dispersing agent include anionic surfactant, nonionic surfactant, cationic surfactant, and amphoteric surfactant. Among the above, the anionic surfactant is especially preferable.

The above high Tg latex can be synthesized with ease by an ordinary emulsification polymerization method. Examples of general emulsification polymerization methods are described in detail in "Synthetic Resin Emulsion (edited by Taira Okuda and Hiroshi Inagaki, published by High Molecule Kanko-kai (a company literally described as High Molecule Publication Association), 1978)," "Application of Synthesized Latex (edited by Takaaki Sugimura, Yasuo Kataoka, Souichi Suzuki and Keiji Kasahara, published by High Molecule Kanko-kai, 1993)," "Chemistry of Synthesized Latex (written by Souichi Muroi, published by High Molecule Kanko-kai, 1970)," and the like.

Hereinafter described in detail is a specific synthesis example of the above high Tg latex.

At first, into a glass autoclave (TEM-V1000 made by Taiatsu Techno), styrene 90 g, acrylic acid 3 g, distilled water 160 g, a surfactant (Sandet BL made by Sanyo Chemical Industries, Ltd.) 2 g are introduced, followed by stirring for 1 hour under a nitrogen airflow. Then, a reaction receptor was sealed and butadiene 7 g was added, followed by temperature increase to 60° C. To the resultant, potassium persulfate water solution (5% by mass) 10 g was added, followed by stirring for 10 hours for reaction. After the reaction, the temperature was decreased to room temperature, followed by adding distilled water 60 g for stirring for 30 minutes, to thereby obtain opalescent liquid latex 327 g. This dispersion solution was a fine latex liquid (average particle diameter 76 nm) containing nonvolatile content 30.2% by mass.

Moreover, another specific synthesis example of the above high Tg latex is described as follows. Into 500 ml three-neck flask provided with a cooling tube and a stirring device, a solution (in which sodium dodecyl sulfate 2 g is dissolved in distilled water 250 ml) was introduced as a surfactant, then, a mixed solution of styrene 80 g, 2-ethyl hexyl acrylate 15 g and acrylic acid 5 g was added, followed by stirring at 200 rpm under a nitrogen airflow. This reaction solution was heated to 75° C., then added by a solution (in which potassium persulfate 0.2 g is dissolved in distilled water 10 mL), to thereby carry out polymerization for 2 hours. Moreover, a solution in which potassium persulfate 0.2 g is dissolved in distilled water 10 mL was added, followed by polymerization for 2 hours. This reaction solution was cooled to the room temperature, then was subjected to a dialysis using a cellulose film having a fraction molecule amount 10,000, followed by removing excessive surfactants and inorganic salts, followed by depression-condensation, followed by removing insoluble content through a filtering, to thereby obtain a dispersion solution 380 g showing fine emulsion white. This dispersion solution was a fine latex liquid (average particle diameter 66 nm) containing nonvolatile content 26.3% by mass.

Herein, the other high Tg latex used for the present invention can be synthesized with ease by a method like the above method.

Amount consumed of the above high Tg latex is preferably 1 g to 20 g per 1 $m^2$ of the gas sensing material, and more preferably 1 g to 15 g. The above high Tg latex may be blended with the other high Tg latex of the present invention, namely, two or more blending is allowed. Moreover, the above high Tg latex may be combined with another latex (which is not contained in the present invention), or with a polymer binder.

The gas sensing material according to the first embodiment and the gas sensing layer may have improved performance in the following cases: i) applying any of the gas sensing material and the gas sensing layer using an application liquid (with 30% by mass or more of solvent being water), followed by drying for formation, ii) any of the binder of the gas sensing material and the gas sensing layer is soluble or dispersible in water solvent, iii) especially, any of the gas sensing material and the gas sensing layer is made of polymer latex having equilibrium water content 2% by mass or less at 25° C.-60% RH. The most preferable is that preparation is made such that ion conductivity is 2.5 mS/cm or less, examples of such preparation method include a refining treatment using separation function film after polymer synthesization.

The water solvent in which the above polymer is soluble or dispersible is a mixture of i) water and ii) an organic solvent 70% by mass or less which has water-mixing property. Examples of the water-mixing organic solvent include alcohols such as methyl alcohol, ethyl alcohol, propyl alcohol and the like; cellosolves such as methyl cellosolve, ethyl cellosolve, butyl cellosolve and the like; ethyl acetate; dimethyl holmiamide; and the like.

When the polymer is not dissolved thermodynamically, namely, when the polymer is present in so-called a dispersion state, the term "water solvent" is to be used herein.

By using a mass $W_1$ of a polymer in adjusted humidity equilibrium under atmosphere of 25° C.-60% RH and a mass $W_0$ of a polymer in a bone dry state at 25° C., the above "equilibrium water content at 25° C.-60% RH" can be obtained by the following equation:

equilibrium water content (% by mass) at 25° C.-60% RH=$((W_1-W_0)/W_0)\times 100$.

The equilibrium water content of the above binder polymer at 25° C.-60% RH is preferably 2% by mass or less, more preferably 0.01% by mass to 1.5% by mass, and especially preferably 0.02% by mass to 1% by mass.

Herein, definition and measuring method of the above water content are described, for example, in High Molecular Engineering Laboratory 14, high molecular material test method (edited by The Society of Polymer Science, Japan, ChijinShokan Co., Ltd.).

Of the present invention, the polymer that is dispersible in water solvent is especially preferable. Examples of the dispersion state include the one in which a latex or a polymer molecule (in which fine particle of a water-insoluble hydrophobic polymer is dispersed) is dispersed in a molecule state or is dispersed by forming micelle, and the like, either of the above is preferable. The dispersion particle has an average particle diameter preferably of 1 nm to 50,000 nm, and 5 nm to 1000 nm is more preferable. The particle diameter distribution of the dispersion particle is not specifically limited, and therefore may be properly selected according to the object, those having a wide particle diameter distribution and those having a single dispersion particle diameter distribution are preferable.

Preferable examples of the polymer dispersible in the above water solvent include hydrophobic polymers such as acrylic polymer, poly(ester)s, rubbers (for example, SBR resin), poly(urethane)s, poly(vinyl chloride)s, poly(vinyl acetate)s, poly(vinylidene chloride)s, poly(oleofine)s, and the like. These polymers may be any of a direct-chain polymer, a branched polymer, a crosslinked polymer, so-called a homopolymer (polymerization of single monomers), a copolymer (polymerization of two or more monomers). The copolymer may be any of a random copolymer and a block copolymer.

The number average molecular weight (Mn) of the above polymer is preferably 5,000 to 1,000,000, and more preferably 10,000 to 200,000. When the above molecule amount is too small, dynamic strength of the emulsion layer may be insufficient, while too high, film forming property may be worse, which are not preferable.

According to the first embodiment of the present invention, the above nonphotosensitive organic silver salt water dispersion solution and the above binder can be mixed for manufacturing the gas sensing material. Herein, mixing two or more organic silver salt water dispersion solutions and two or more binders is preferable.

In this case, the nonphotosensitive heat developing liquid is to be directly applied to the inspection object, followed by drying and still followed by peeling, to thereby carry out the heat developing treatment.

Specific examples of the above applying method include extrusion coating, slide coating, curtain coating, dip coating, knife coating, flow coating. Moreover, the following operations are included in the specific examples: various coating operations including the extrusion coating using various hoppers described in U.S. Pat. No. 2,681,294, any of the extrusion coating and the slide coating described at page 399 to page 536 "LIQUID FILM COATING" (CHAPMAN & amp; published by HALL, 1997) written by Stephen F. Kistler, Petert M. Schweizer is preferably used, and especially preferable is the slide coating.

An example of the shape of the slide coater used for the above slide coating is described in FIG. 11b. 1 at page 427 of "LIQUID FILM COATING" (CHAPMAN & amp; published by HALL, 1997) written by Stephen F. Kistler, Petert M. Schweizer. Moreover, when desired, any of the methods described at page 399 to page 536 of "LIQUID FILM COAT-ING" (CHAPMAN & amp; published by HALL, 1997) written by Stephen F. Kistler, Petert M. Schweizer, in the U.S. Pat. No. 2,761,791, and in Great Britain Patent No. 837,095 may be used for simultaneously coating two layers or more.

Moreover, according to the second embodiment of the present invention, an application liquid is applied on to a support, which application liquid is a mixture of the above nonphotosensitive organic silver salt water dispersion solution and the above binder, to thereby manufacture the sheet-shaped application matter.

In this case, the sheet-shaped application matter is sealably attached to the inspection object for measurement, and can thereafter be subjected to a heat developing treatment.

It is preferable that the sheet-shaped application matter has an adhesive layer, and is thereby adhered to the inspection object via the adhesive layer. In the case of the sheet-shaped application matter, the time for the inspection can be decreased, and no expert skill is necessary due to an easy inspection. Moreover, the application amount of the nonphotosensitive heat developing liquid becoming constant can improve accuracy and reproducibility of the inspection. Measuring developing quantity of the above organic silver salt can accomplish a quantitative measurement.

Heat developer

Examples of the above heat developer include a reducing agent for the above nonphotosensitive organic silver salt. The reducing agent for the nonphotosensitive organic silver salt may be an arbitrary material which reduces silver ion to metal silver, preferably an organic material.

Examples of the above reducing agent include those described in JP-A No. 11-65021 (paragraph No. 0043 to paragraph No. 0045), EP0803764A1 (line 34 at page 7 to line 18 at page 12). Among the above, any of hindered phenols reducing agent and bisphenols reducing agent are preferable, and the compound expressed by the following formula (1) is especially preferable.

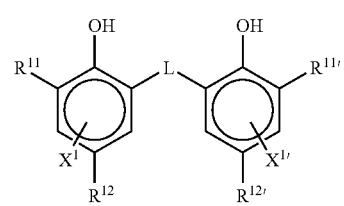

Formula (1)

In the above formula (1), $R^{11}$ and $R^{11'}$ each denote an alkyl group having 1 to 20 carbon atoms. $R^{12}$ and $R^{12'}$ each denote i) a hydrogen atom or ii) a substitutional group which is substitutable with benzene ring. L denotes —S-group or —$CHR^{13}$-group (where $R^{13}$ denotes i) hydrogen atom or ii) an alkyl group which has 1 to 20 carbon atoms). $X^1$ and $X^{1'}$ each denote i) a hydrogen atom or ii) a substitutional group which is substitutable with benzene ring.

$R^{11}$ and $R^{11'}$ each denote an alkyl group which is substitutional or nonsubstitutional and has 1 to 20 carbon atoms. The substitutional group of the alkyl group is not specifically limited, and therefore may be properly selected according to the object, examples thereof including aryl group, hydroxy group, alkoxy group, aryloxy group, alkylthio group, arylthio group, acylamino group, sulfone amide group, sulfonyl group, phosphoryl group, acyl group, carbamoyl group, ester group, halogen atom, and the like. Among the above, the secondary and tertiary alkyl groups each having 3 to 15 carbon atoms are preferable, examples thereof including isopropyl group, isobutyl group, t-butyl group, t-amyl group, t-octyl group, cyclohexyl group, cyclopentyl group, 1-methyl cyclohexyl group, 1-methyl cyclo propyl group, and the like. Among the above, the tertiary alkyl group having 4 to 12 carbon atoms is preferable, preferable examples of the tertiary alkyl group including t-butyl group, t-amyl group, 1-methyl cyclohexyl group, and especially preferably t-butyl group.

$R^{12}$ and $R^{12'}$ each denote i) a hydrogen atom or ii) a substitutional group which is substitutable with benzene ring.

Examples of the substitutional group which is substitutable with the above benzene ring include alkyl group, aryl group, halogen atom, alkoxy group, acylamino group, and the like. Among the above, the alkyl group having 1 to 20 carbon atoms is preferable.

Examples of the alkyl group include methyl group, ethyl group, propyl group, butyl group, isopropyl group, t-butyl group, t-amyl group, cyclohexyl group, 1-methyl cyclohexyl group, benzil group, methoxy methyl group, methoxy ethyl group, and the like. Among the above, methyl group, ethyl group, propyl group, isopropyl group, and t-butyl group are especially preferable.

$X^1$ and $X^{1'}$ each denote i) a hydrogen atom or ii) a substitutional group which is substitutable with benzene ring. The substitutional group which is substitutable with the above benzene ring are same as those described above. Among the above, hydrogen atom, halogen atom, and alkyl group are preferable, and hydrogen atom is more preferable.

L denotes —S-group or —$CHR^{13}$-group (where $R^{13}$ denotes i) hydrogen atom or ii) alkyl group having 1 to 20 carbon atoms).

$R^{13}$ denotes i) hydrogen atom or ii) alkyl group having 1 to 20 carbon atoms. The alkyl group may have a substitutional group. Examples of the alkyl group include methyl group, ethyl group, propyl group, butyl group, heptyl group, undecyl group, isopropyl group, 1-ethyl pentyl group, 2,4,4-trimethyl pentyl group, and the like.

The substitutional group of the above alkyl group is preferably like the one of substitutional group of the above $R^{11}$, examples thereof including halogen atom, alkoxy group, alkylthio group, aryloxy group, arylthio group, acylamino group, sulfone amide group, sulfonyl group, phosphoryl group, oxycarbonyl group, carbamoyl group, sulfamoyl group, and the like. Among the above, —$CHR^{13}$-group is preferable. $R^{13}$ is i) hydrogen atom or ii) alkyl group having 1 to 15 carbon atoms. Preferable examples of the alkyl group include methyl group, ethyl group, propyl group, isopropyl group, and 2,4,4-trimethyl pentyl group. Among the above, any of hydrogen atom, methyl group, propyl group, and isopropyl group are especially preferable.

When $R^{13}$ is hydrogen atom, $R^{12}$ and $R^{12'}$ each are preferably an alkyl group having 2 to 5 carbon atoms, more preferably ethyl group and propyl group, and most preferably ethyl group.

When $R^{13}$ is a primary or a secondary alkyl group having 1 to 8 carbon atoms, $R^{12}$ and $R^{12'}$ each are preferably methyl group. The primary or secondary alkyl group of $R^{13}$ having 1 to 8 carbon atoms is preferably methyl group, ethyl group, propyl group, and isopropyl group, and more preferably methyl group, ethyl group, and propyl group. When each of $R^{11}$, $R^{11'}$, $R^{12}$ and $R^{12'}$ is methyl group, $R^{13}$ is preferably a secondary alkyl group. In this case, the secondary alkyl group of $R^{13}$ is preferably isopropyl group, isobutyl group, and 1-ethyl pentyl group, and more preferably isopropyl group.

Hereinafter described are specific examples of the reducing agent of the present invention, firstly including the compound expressed by the above formula (1), the present invention is, however, not limited thereto. Among the above, especially, the compounds expressed by (I-1) to (I-27) are preferable.

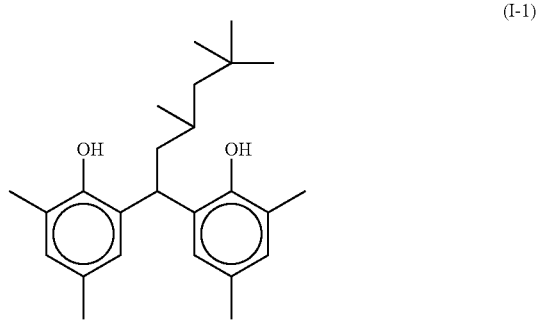

(I-1)

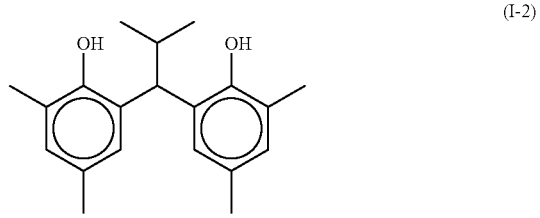

(I-2)

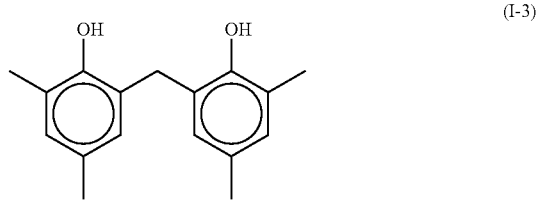

(I-3)

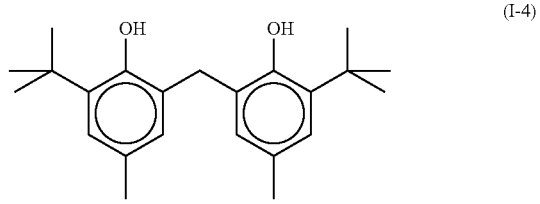

(I-4)

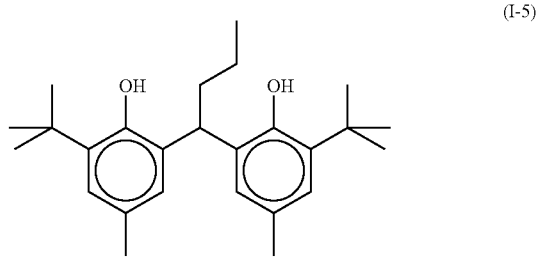

(I-5)

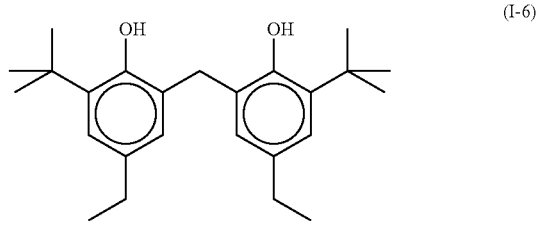

(I-6)

-continued
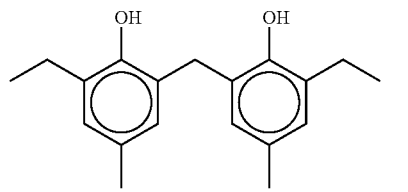
(I-7)
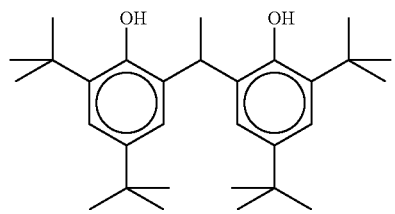
(I-8)
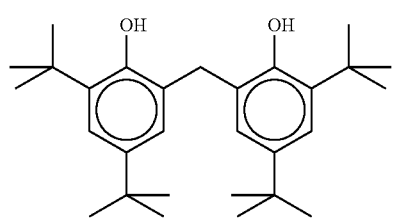
(I-9)
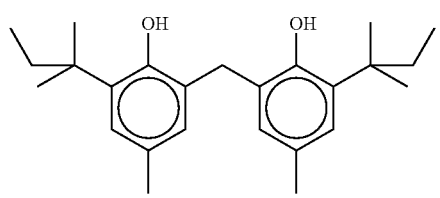
(I-10)
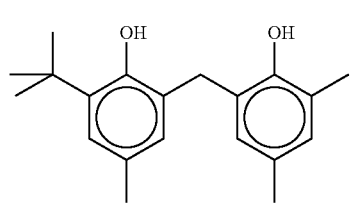
(I-11)
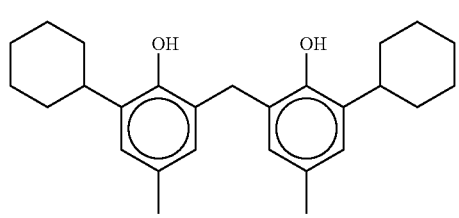
(I-12)
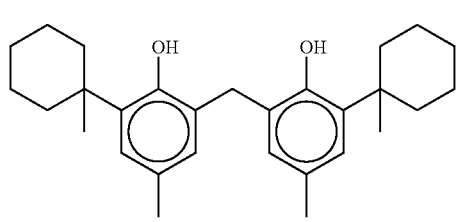
(I-13)
-continued
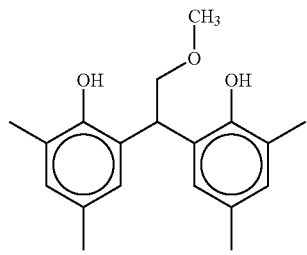
(I-14)
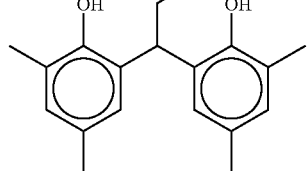
(I-15)
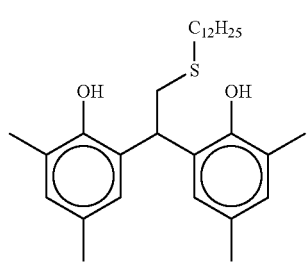
(I-16)
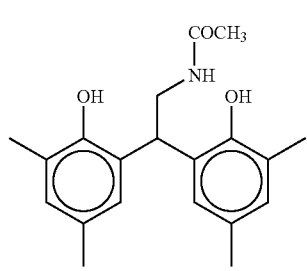
(I-17)
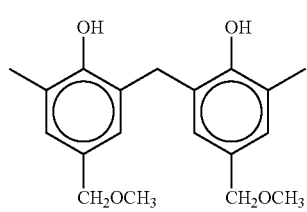
(I-18)
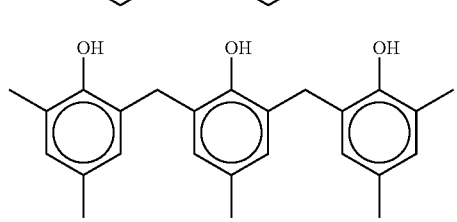
(I-19)

-continued (I-20)
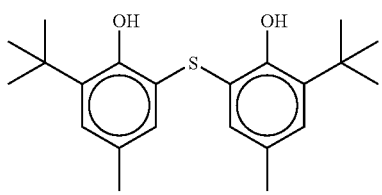

(I-21)
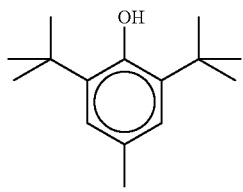

(I-22)
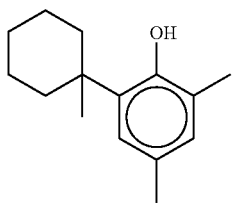

(I-23)
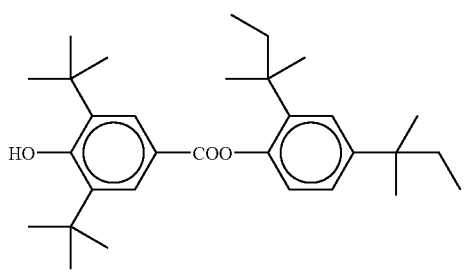

(I-24)
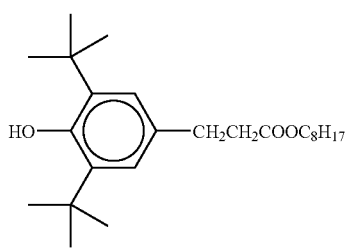

(I-25)
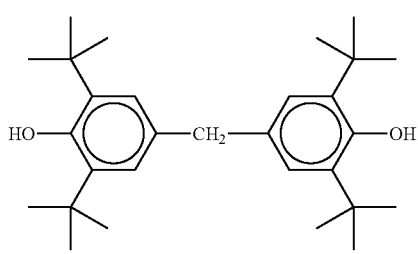

(I-26)
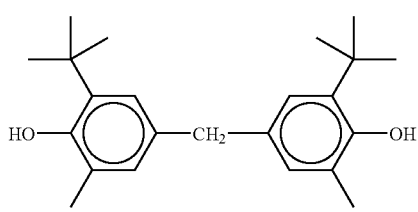

-continued (I-27)
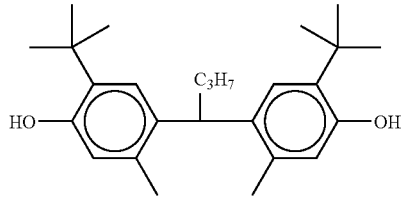

Content of the above reducing agent is preferably 0.01 g/m² to 5.0 g/m², and more preferably 0.1 g/m² to 3.0 g/m². The above reducing agent is preferably contained by 5% by mol to 50% by mol relative to the silver 1 mol of the above gas sensing material (or gas sensing layer), and more preferably 10% by mol to 40% by mol.

By any of the methods including solution mode, emulsification dispersion mode, solid fine particle dispersed matter mode and the like, the above reducing agent may be contained in the application liquid and contained in the photosensitive material. Examples of known emulsifying-dispersing method include a method carrying out dissolution by using the following auxiliary solvents, to thereby mechanically prepare an emulsified-dispersed matter: oils such as dibutyl phthalate, tricresyl phosphate, glyceryl triacetate, diethyl phthalate, and the like; ethyl acetate; cyclohexanone; and the like.

In the above solid fine particle dispersing method, the reducing agent powder is to be dispersed in a proper solvent such as water and the like, by means of any of a ball mill, a colloid mill, a vibration ball mill, a sand mill, a jet mill, a roller mill and a supersonic wave, to thereby form a solid dispersed matter. In this case, a protective colloid (for example, polyvinyl alcohol) and a surfactant (for example, an anionic surfactant such as triisopropyl naphthalene sodium sulfonate (a mixture of three isopropyl groups having different substitutional positions)) may be used. The water dispersed matter may contain rust-preventive (for example, benzoisothiazorinone sodium salt).

Together with the above heat developer, and in addition, each of the gas sensing material according to the first embodiment and the above gas sensing layer is preferably combined with a development promoter. Preferably used development promoters include a phenol derivative expressed by the following formula (2).

Formula (2)
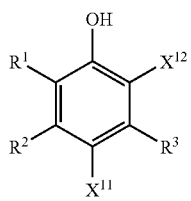

In the above formula (2), $R^1$, $R^2$, $R^3$, $X^{11}$, and $X^{12}$ each denote any of hydrogen atom, halogen atom, and a substitutional group (which is bonded to benzene ring by any of carbon atom, oxygen atom, nitrogen atom, sulfur atom and phosphor atom). Hereinabove, at least one of $X^{11}$ and $X^{12}$ is a group expressed by —$NR^4R^5$. $R^4$ and $R^5$ each are hydrogen atom, alkyl group, alkenyl group, alkynyl group, aryl group, and heterocyclic group. Otherwise, $R^4$ and $R^5$ each are a group expressed by any of —C (=O)—R, —C (=O)—C (=O)—R, —SO₂—R, —SO—R, —P (=O) (R)₂ and —C (=NR')—R. R and R' each are a group selected from any of hydrogen atom, alkyl group, aryl group, heterocyclic group, amino group, alkoxy group, and aryloxy group. In the above substitutional groups, adjacent groups may be so bonded as to form a ring.

When the above reducing agent has an aromatic hydroxyl group (—OH), especially the above bisphenols, it is preferable to combine an irreducible compound having a group which is capable of forming a hydrogen bond with these groups. Examples of the group capable of forming the hydrogen bond with the above hydroxyl group or amino group include phosphoryl group, sulfoxide group, sulfonyl group, carbonyl group, amide group, ester group, urethane group, ureido group, tertiary amino group, nitrogen-contained aromatic group, and the like. Among the above, compounds having the following are preferable: phosphoryl group, sulfoxide group, amide group (which is free from >N—H group, and is blocked like >N—Ra (where Ra denotes a substitutional group other than hydrogen atom)), urethane group (which is free from >N—H group, and is blocked like >N—Ra (where Ra denotes a substitutional group other than hydrogen atom)), ureido group (which is free from >N—H group, and is blocked like >N—Ra (where Ra denotes a substitutional group other than hydrogen atom)).

As the hydrogen bonding compound, the one expressed by the following formula (3) is preferable.

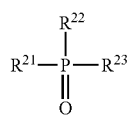

Formula (3)

In the above formula (3), $R^{21}$ to $R^{23}$ each denote any of alkyl group, aryl group, alkoxy group, aryloxy group, amino group, and heterocyclic group. These groups may have non-substitutional group or substitutional group.

Examples of $R^{21}$ to $R^{23}$ which is a substitutional group having substitutional group include halogen atom, alkyl group, aryl group, alkoxy group, amino group, acyl group, acylamino group, alkylthio group, arylthio group, sulfone amide group, acyloxy group, oxycarbonyl group, carbamoyl group, sulfamoyl group, sulfonyl group, phosphoryl group, and the like. Among the above, alkyl group, aryl group, alkoxy group, and aryloxy group are preferable. Moreover, in terms of the effect of the present invention, at least one of $R^{21}$ to $R^{23}$ is preferably alkyl group or aryl group, more preferably two or more of $R^{21}$ to $R^{23}$ are alkyl group or aryl group. Moreover, in terms of availability at cheap cost, $R^{21}$ to $R^{23}$ are preferably the same groups.

Examples of the above alkyl group include methyl group, ethyl group, butyl group, octyl group, dodecyl group, isopropyl group, t-butyl group, t-amyl group, t-octyl group, cyclohexyl group, 1-methyl cyclohexyl group, benzil group, phenethyl group, 2-phenoxy propyl group, and the like.

Examples of the above aryl group include phenyl group, cresyl group, xylyl group, naphthyl group, 4-t-butyl phenyl group, 4-t-octyl phenyl group, 4-anicidyl group, 3,5-dichlorophenyl group, and the like.

Examples of the above alkoxy group include methoxy group, ethoxy group, butoxy group, octyloxy group, 2-ethyl hexyloxy group, 3,5,5-trimethyl hexyloxy group, dodecyloxy group, cyclohexyloxy group, 4-methyl cyclohexyloxy group, benzil oxy group, and the like.

Examples of the above aryloxy group include phenoxy group, cresyl oxy group, isopropyl phenoxy group, 4-t-butyl phenoxy group, naphthoxy group, biphenyloxy group, and the like. Examples of the above amino group include dimethyl amino group, diethyl amino group, dibutyl amino group, dioctyl amino group, N-methyl-N-hexyl amino group, dicyclohexyl amino group, diphenyl amino group, N-methyl-N-phenyl amino group, and the like.

Hereinafter described are specific examples of the compound having the hydrogen bonding property, firstly including the compound expressed by the above formula (3), the present invention is, however, not limited thereto.

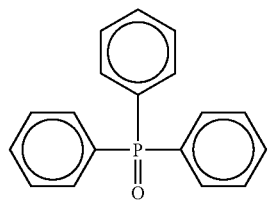
(II-1)

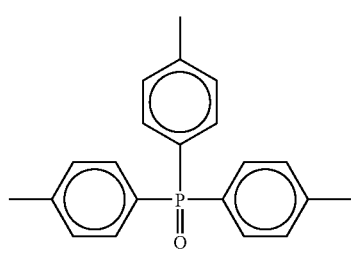
(II-2)

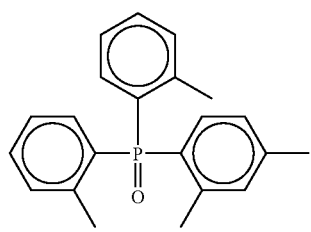
(II-3)

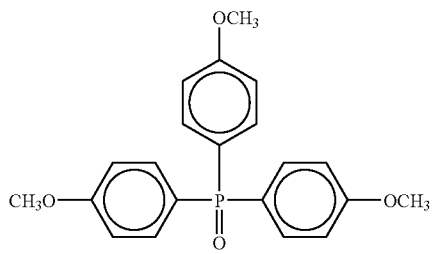
(II-4)

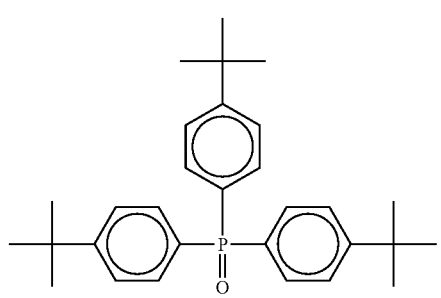
(II-5)

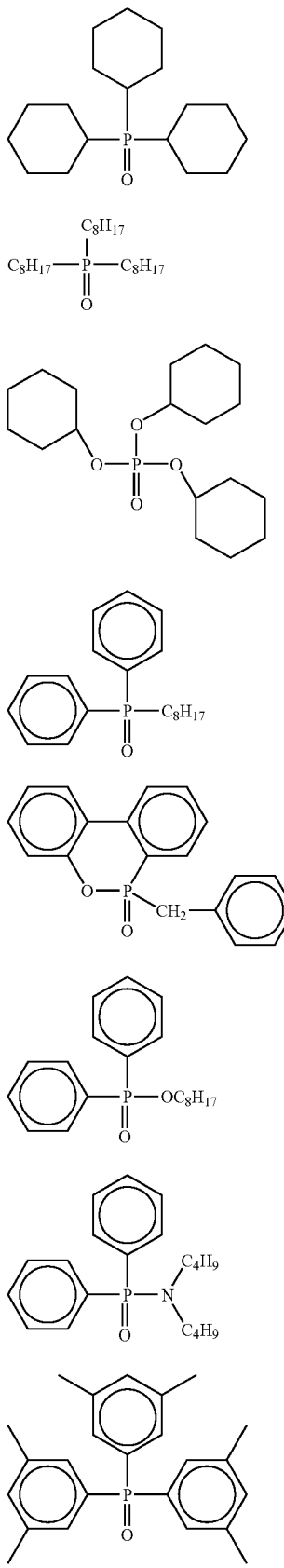
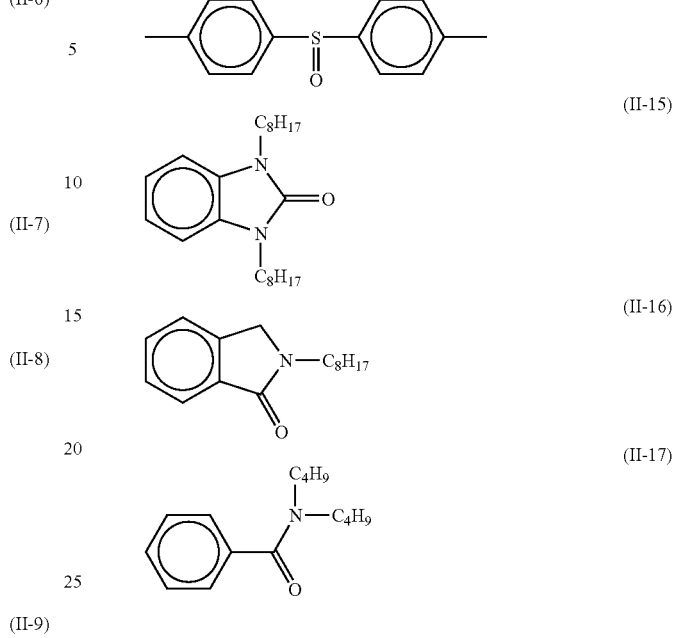

Examples of the above hydrogen bonding compound include, other than those described above, those described in JP-A No. 2001-281793, JP-A No. 2002-014438, and the like.

Like the reducing agent, the compounds of the above formula (3) may be contained in an application liquid in any of a solution mode, an emulsification dispersion mode, and a solid dispersion fine particle dispersed matter mode, and may be used in the gas sensing material. The above hydrogen bonding compound forms a hydrogen bonding complex, in a solution state, with a compound having phenol hydroxyl group and amino group. The above hydrogen bonding compound can be isolated as a complex in a crystal state, depending on the combination of the above reducing agent and the compound of the above formula (3).

The thus isolated crystal powder used as a solid dispersion fine particle dispersed matter is especially preferable for obtaining stable performance. Moreover, the following method is preferably used: mixing the above reducing agent and the compound of the above formula (3) with a powder, and forming the complex in the dispersing by means of a sand grinder mill and the like by using a proper dispersing agent.

Content of the compound in the formula (3) is not specifically limited, and therefore can be properly determined according to the reducing agent and the like.

Other Components

The solvent (for convenience sake, the solvent and the dispersion medium are, in combination, referred to as solvent) of the application liquid used for the gas sensing material according to the first embodiment and the above gas sensing layer is preferably a water solvent which contains water 30% by mass or more. Examples of component other than water include hexane, cyclohexane, toluene, methanol, ethanol, isopropanol, acetone, methyl ethyl ketone, ethyl acetate, 1,1,1-trichloroethane, tetrahydrofuran, triethyl amine, thiophene, trifluoroethanol, perfluoropentane, xylene, n-butanol, phenol, methyl isobutyl ketone, cyclohexanone, butyl acetate, diethyl carbonate, chlorobenzene, dibutyl ether, anisole, ethylene glycol diethyl ether, N,N-dimethyl formamide, morpholine, propane sultone, perfluorotributyl amine, methyl cello solve, ethyl cellosolve, dimethyl formamide, and the like.

Water content of the above solvent is preferably 50% by mass or more, and more preferably 70% by mass or more. Preferable examples of the solvent composition include, other than water, water/methyl alcohol=90% by mass/10% by mass, water/methyl alcohol=70% by mass/30% by mass, water/methyl alcohol/dimethyl formamide=80% by mass/15% by mass/5% by mass, water/methyl alcohol/ethyl cellosolve=85% by mass/10% by mass/5% by mass, water/methyl alcohol/isopropyl alcohol=85% by mass/10% by mass/5% by mass, and the like.

Examples of the fogging preventive, stabilizer and stabilizer precursor which are used for the gas sensing material according to the first embodiment and the above gas sensing layer include the compounds described in JP-A No. 10-62899 (paragraph No. 0070), EP0803764A1 (line 57 at page 20 to line 7 at page 21), JP-A No. 9-281637, and JP-A No. 9-329864.

As the above fogging preventive, an organic polyhalide can be contained, and containing a proper amount of polyhalogen compound can bring about an improved effect of a remarkable image preservability. In terms of the above, JP-A No. 11-65021 (paragraph No. 0111 to paragraph No. 0112) make a description. Among the above, especially, the organic halogen compound expressed by the formula (P) in JP-A No. 2000-284399, the organic polyhalogen compound expressed by the general formula (II) in JP-A No. 10-339934, and the organic polyhalogen compound described in JP-A No. 2001-033911 are preferable.

As the above organic polyhalogen compound, a compound expressed by the following formula (4) is preferable.

$$Q\text{-}(Y)_n\text{—}C(Z^1)(Z^2)X \quad \text{Formula (4)}$$

In the above formula (4), Q denotes any of an alkyl group, an aryl group, and a heterocyclic group. Y denotes a divalent bonding group. n denotes 0 or 1. $Z^1$ and $Z^2$ each denote a halogen atom. X denotes one of a hydrogen atom and an electron absorbing group.

In the above formula (4), Q denotes a phenyl group substituted with an electron absorbing group which has Hammett's substitutional group constant σp of positive value. In terms of the Hammett's substitutional group constant, Journal of Medicinal Chemistry, 1973, Vol. 16, No. 11, pp. 1207-1216 and the like may be referred.

Examples of the above electron absorbing group include halogen atom (fluorine atom (σp value: 0.06), chlorine atom σp value: 0.23), bromine atom (σp value: 0.23), iodine atom (σvalue: 0.18)), trihalomethyl group (tribromomethyl (σp value: 0.29), trichloromethyl (σp value: 0.33), trifluoromethyl (σp value: 0.54)), cyano group (σp value: 0.66), nitro group (σp value: 0.78), aliphatic-aryl or heterocyclic ring sulfonyl group (for example, methane sulfonyl (σp value: 0.72)), aliphatic-aryl or heterocyclic ring acyl group (for example, acetyl (σp value: 0.50), benzoyl (σp value: 0.43)), alkynyl group (for example, C≡CH (σp value: 0.23)), aliphatic-aryl or heterocyclic ring oxycarbonyl group (for example, methoxycarbonyl (σp value: 0.45), phenoxycarbonyl (σp value: 0.44)), carbamoyl group (σp value: 0.36), sulfamoyl group (σp value: 0.57), sulfoxide group, heterocyclic group, phosphoryl group, and the like.

The above Hammett's substitutional group constant σp value is preferably 0.2 to 2.0, and more preferably 0.4 to 1.0.

Preferable examples of the above electron absorbing group include carbamoyl group, alkoxycarbonyl group, alkyl sulfonyl group, alkyl phosphoryl group, and the like. Among the above, carbamoyl group is the most preferable.

In the above formula (4), X is preferably an electron absorbing group, more preferably halogen atom, aliphatic-aryl or heterocyclic ring sulfonyl group, aliphatic-aryl or heterocyclic ring acyl group, aliphatic-aryl or heterocyclic ring oxycarbonyl group, carbamoyl group and sulfamoyl group, and especially preferably halogen atom. Among the halogen atoms, chlorine atom, bromine atom and iodine atom are preferable, chlorine atom and bromine atom are more preferable, and bromine atom is especially preferable.

In the above formula (4), Y is preferably any of —C(=O)— and —SO— and —SO$_2$—, more preferably any of —C(=O)— and —SO$_2$—, and especially preferably —SO$_2$—. n denotes 0 or 1, preferably 1.

Hereinafter described are specific examples of compound of the above formula (4), the present invention is, however, not limited thereto.

(III-1)

(III-2)

(III-3)

(III-4)

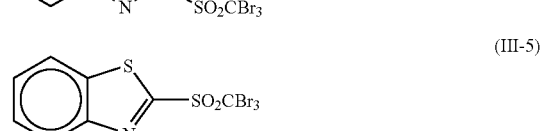

(III-5)

(III-6)

(III-7)

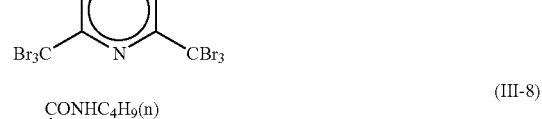

(III-8)

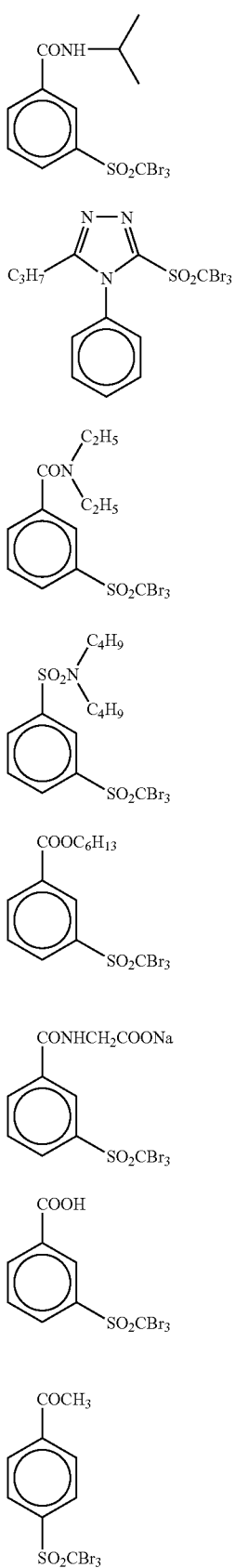
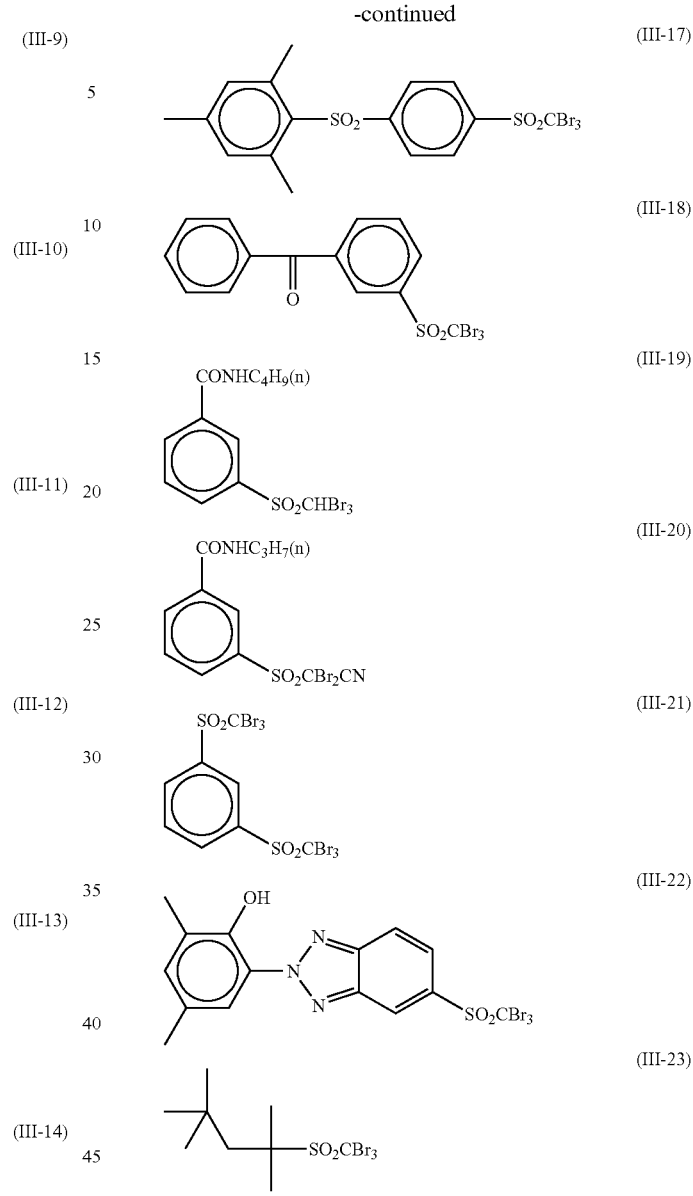

Relative to the above nonphotosensitive organic silver salt 1 mol, the amount consumed of the compound expressed by the above formula (4) is preferably $1^{-3}$ mol to 0.8 mol, more preferably $10^{-3}$ mol to 0.1 mol, and especially preferably $5 \times 10^{-3}$ mol to 0.05 mol.

An example of a method of containing the above fogging preventive in the gas sensing material and the gas sensing layer include the one described in the above method of containing the reducing agent. The above organic polyhalogen compound may be preferably be added by the solid fine particle dispersed matter.

Examples of the other fogging preventive include the mercury (II) salt of JP-A No. 11-65021 (paragraph No. 0113), the benzoic acids of JP-A No. 11-65021 (paragraph No. 0114), the salicylic acid derivative of JP-A No. 2000-206642, the formalin scavenger compound expressed by the formula (S) of JP-A No. 2000-221634, the triazine compound according to claim 9 of JP-A No. 11-352624, the compound expressed by the general formula (III) of JP-A No. 6-11791, 4-hydroxy-6-methyl-1,3,3a,7-tetrazaindene, and the like.

For preventing the fogging, any of the gas sensing material according to the first embodiment and the above gas sensing layer may contain azolium salt. Examples of the azolium salt include the compound expressed by the general formula (XI) of JP-A No. 59-193447, the compound described in Japanese Patent Application Publication (JP-B) No. 55-12581, and the compound expressed by the general formula (II) of JP-A No. 60-153039. The above azolium salt may be added to any part of the gas sensing material, preferably however, to the above gas sensing layer. Timing for adding the above azolium salt may be in any of the operations for preparing the application liquid. In the case of adding the azolium salt to the above gas sensing layer, the above timing may be in any of the operations from the organic silver salt preparation to the application liquid preparation, in this case however, a period from immediately after the organic silver salt preparation to on the eve of the application is preferable. The above azolium salt adding method may be any of those using powder, solution, fine particle dispersed matter, and the like. Moreover, solution mixture of other additives such as sensitizing pigment, reducing agent, color toning agent and the like may be added.

Addition amount of the above azolium salt is not specifically limit, and therefore may be properly selected according to the object, for example, $1\times10^{-6}$ mol to 2 mol per silver 1 mol is preferable, and $1\times10^{-3}$ mol to 0.5 mol is more preferable.

For controlling development by suppressing or by promoting the development and for improving preservability before and after the development, the gas sensing material according to the first embodiment and the above gas sensing layer may contain mercapto compound, disulfide compound, and thion compound. The above is described in JP-A No. 10-62899 (paragraph No. 0067 to paragraph No. 0069), the compound expressed by the general formula (I) and paragraph No. 0033 to paragraph No. 0052 of JP-A No. 10-186572, EP0803764A1 (line 36 to line 56 at page 20), JP-A No. 2001-100358, and the like. Among the above, the mercapto substitutional complex aromatic compound is especially preferable.

The gas sensing material according to the first embodiment and the above gas sensing layer may contain color toning agent. The above color toning agent is described in JP-A No. 10-62899 (paragraph No. 0054 to paragraph No. 0055), EP0803764A1 (line 23 to line 48 at page 21), and JP-A No. 2000-356317. Among the above, especially, phthalazinones (phthaladinone, phthaladinone derivative or metal salt (for example, 4-(1-naphthyl) phthaladinone, 6-chlorophthaladinone, 5, 7-dimethoxy phthaladinone and 2,3-dihydro-1,4-phthalazine dion)); a combination of phthalazinones and phthalic acids (for example, phthalic acid, 4-methyl phthalic acid, 4-nitrophthalic acid, diammonium phthalate, sodium phthalate, potassium phthalate and tetrachloro phthalic anhydride); phthalazines (phthalazine, phthalazine derivative or metal salt; for example, 4-(1-naphthyl) phthalazine, 6-isopropyl phthalazine, 6-t-butyl phthaladine, 6-chlorophthalazine, 5,7-dimethoxy phthalazine and 2, 3-dihydrophthalazine); and a combination of phthalazines and phthalic acids are preferable. The combination of the phthalazines and the phthalic acids is especially preferable.

Addition amount of the above phthalazines per the above organic silver salt 1 mol is preferably 0.01 mol to 0.3 mol, more preferably 0.02 mol to 0.2 mol, and especially preferably 0.02 mol to 0.1 mol.

The plasticizer and the lubricant used for the gas sensing material according to the first embodiment and the above gas sensing layer are described in JP-A No. 11-65021 (paragraph No. 0117). A cementing agent for forming a cemented image, adding method thereof and adding amount thereof are described in JP-A No. 11-65021 (paragraph No. 0118); JP-A No. 11-223898 (paragraph No. 0136 to paragraph No. 0193); and the formula (H), the formula (1) to the formula (3), the compounds of the formula (A) and the formula (B) of JP-A No. 2000-284399. The hardening promoter is described in JP-A No. 11-65021 (paragraph No. 0102), JP-A No. 11-223898 (paragraph No. 0194 to paragraph No. 0195), and the like.

When using the above cementing agent for any of the gas sensing material according to the first embodiment and the above gas sensing layer, an acid made by hydration of diphosphate pentoxide or the salt thereof may be preferably combined. Examples of the acid made by hydration of diphosphate pentoxide or the salt thereof include metaphosphoric acid (salt), pyrophoric acid (salt), orthophosphoric acid (salt), triphosphate (salt), tetraphosphate (salt), hexametaphosphoric acid (salt), and the like. Especially preferable of the above are orthophosphoric acid or a salt thereof, hexametaphosphoric acid or a salt thereof, and the like. Specific examples include sodium orthophosphate, sodium dihydrogen orthophosphate, sodium hexametaphosphate, ammonium hexametaphosphate, and the like.

Amount consumed (application amount per photosensitive material 1 $m^2$) of the acid made by hydration of diphosphate pentoxide or the salt thereof may be desirably determined according to the performance such as fogging, preferably 0.1 $mg/m^2$ to 500 $mg/m^2$, and more preferably 0.5 $mg/m^2$ to 100 $mg/m^2$.

For improving conveying property, any of the gas sensing material according to the first embodiment and the above gas sensing layer may be preferably added by a matting agent. The matting agent is generally fine particle of a water-insoluble organic compound or a water-insoluble inorganic compound. The matting agent may be arbitrarily selected, examples thereof including those known in the art such as: i) organic matting agents described in U.S. Pat. Nos. 1,939,213, 2,701,245, 2,322,037, 3,262,782, 3,539,344, 3,767,448, and the like; and ii) inorganic matting agents described in U.S. Pat. Nos. 1,260,772, 2,192,241, 3,257,206, 3,370,951, 3,523, 022, 3,769,020 and the like.

Examples of the organic compound used for the above matting agent include water-dispersive vinyl polymer, cellulose derivative, starch derivative, and the like. Moreover, i) a gelatin hardened with a known hardener and having a fine capsule hollow grain and ii) a gelatin hardened with a coacervate and having a fine capsule hollow grain are preferably used. Examples of the above water-dispersive vinyl polymer include polymethyl acrylate, polymethyl methacrylate, polyacrylonitrile, acrylonitrile-α-methyl styrene copolymer, polystyrene, styrene-divinyl benzene copolymer, polyvinyl acetate, polyethylene carbonate, polytetrafluoroethylene, and the like.

Examples of the above cellulose derivative include methyl cellulose, cellulose acetate, cellulose acetate propionate and the like. Examples of the above starch derivative include carboxy starch, carboxy nitrophenyl starch, carbamide-formaldehyde-starch reactant, and the like.

Preferable examples of the inorganic compound used for the above matting agent include silicon dioxide, titanium dioxide, magnesium dioxide, aluminum oxide, barium sulfate, calcium carbonate, silver chloride (desensitized by a known method), silver bromide (desensitized by a known method), glass, diatomaceous earth, and the like.

When necessary, the above matting agent may be mixed with different materials. The scale and shape of the matting agent are not specifically limited, and therefore an arbitrary particle diameter may be use. For carrying out the present invention, particle diameter 0.1 μm to 30 μm is preferable. Moreover, particle diameter distribution of the matting agent may be small or large. On the other hand, the above matting agent which is largely influenced by haze and surface gloss of a sensitizing material is preferred to have proper particle diameter, proper shape and proper particle diameter distribution according to necessity, in the preparation of the matting agent or by mixing a plurality of the matting agents.

The above matting agent is preferably contained in any of i) an outermost surface layer of the gas sensing material, ii) a layer functioning as the outermost surface layer, and iii) a near the layer outer surface, moreover, is preferably contained in a layer operating as so-called a surface protective layer.

The application amount of the above matting agent per the above gas sensing material 1 $m^2$ is preferably 1 mg/$m^2$ to 400 mg/$m^2$, and more preferably 5 mg/$m^2$ to 300 mg/$m^2$.

For improving applying property, charge and the like, the gas sensing material according to the first embodiment and the above gas sensing layer may use surfactant.

Any surfactants may be properly used, including a non-ionic surfactant, an anionic surfactant, a cationic surfactant, and a fluorine surfactant. Specific examples of the surfactant include the fluorine high molecular surfactants described in JP-A No. 62-170950, U.S. Pat. No. 5,380,644 and the like; the fluorine surfactants described JP-A No. 60-244945, JP-A No. 63-188135 and the like; the polysiloxane surfactants described in U.S. Pat. No. 3,885,965 and the like; the poly-alkylene oxide, anionic surfactant and the like described in JP-A No. 6-301140, and the like.

When necessary, the gas sensing material according to the first embodiment and the above gas sensing layer may be added by oxidation preventive, stabilizer, plasticizer, ultra-violet-ray absorber, and coating assistant. The above various additives are described in International Publication No. WO98/36322, EP803764A1, JP-A No. 10-186567, JP-A No. 10-18568, and the like.

For improving film forming property, the gas sensing material of the present invention may be preferably subjected to heat treatment immediately after applying and drying. The heat treatment temperature, namely, film face temperature is preferably 60° C. to 100° C., and heating period is preferably 1 second to 60 seconds. More preferably, the film face temperature is 70° C. to 90° C., and the heating period is 2 seconds to 10 seconds. The above heat treatment method is described in JP-A No. 2002-107872.

The gas sensing material according to the second embodiment of the present invention has at least a support and a gas sensing layer which is located on the support and contains a nonphotosensitive organic silver salt. The gas sensing material according to the second embodiment of the present invention may have other layers properly selected when necessary, examples thereof including surface protective layer, back layer, cushion layer, charge regulating (preventing) layer, reflective layer, color taste preparing layer, preservability improving layer, adhesion preventing layer, anti-curl layer, smoothing layer, and the like. Each of the above layers may be of a single layer structure, or of a laminated layer structure.

The above gas sensing layer has such a structure that one or more layers are located on the support, and as described above, containing the nonphotosensitive organic silver salt, the heat developer and the binder, and further containing, when necessary.

Moreover, the gas sensing layer contains other components such as a color toning agent, a coating assistant and other auxiliary agent, and the like.

Support

The above support is preferably a cloth support, a paper support, a plastic film support, and the like. Herein, the support may be transparent or opaque, being transparent is however, preferable.

Examples of the above plastic film support include polyester film, undercoat polyester film, poly(ethylene terephthalate) film, polyethylene naphthalate film, cellulose nitrate film, cellulose ester film, poly(vinyl acetal) film, polycarbonate film, and the like. Among the above, for eliminating heat contraction strain (caused in the heat developing treatment) by relieving an inner strain remaining in the film in a 2-axis extending operation, a polyester subjected to a heat treatment at 130° C. to 185° C. is preferable, and polyethylene terephthalate is especially preferable.

For the above support, using undercoat technologies is preferable such as the water-soluble polyester of JP-A No. 11-84574, the styrene butadiene copolymer of JP-A No. 10-186565, the vinylidene chloride copolymer of JP-A No. 2000-39684, and the like. Moreover, for any of the charge preventing layer and the undercoat, the technologies described in JP-A No. 56-143430, JP-A No. 56-143431, JP-A No. 58-62646, JP-A No. 56-120519, JP-A No. 11-84573 (paragraph No. 0040 to paragraph No. 0051), U.S. Pat. No. 5,575,957, JP-A No. 11-223898 (paragraph No. 0078 to paragraph No. 0084) may be used.

Surface Protective Layer

For preventing adhesion of the above gas sensing layer, the above surface protective layer may be provided. The surface protective layer may be a single layer or a pliability of layers.

The binder of the above surface protective layer is not specifically limited, and may be made of any polymers, preferably containing a polymer 5 mg/$m^2$ to 100 mg/$m^2$ having carboxylic acid remaining group. Content of the carboxy remaining group of the above polymer is preferably 1.4 mmol to 10 mmol per the above polymer 100 g. Moreover, the carboxylic acid remaining group may form a salt in combination with alkali metal ion, alkali earth metal ion, organic cation, and the like.

Examples of the polymer having the above carboxyl remaining group include a natural high molecule (gelatin, alginic acid, and the like), a modified natural high molecule (carboxy methyl cellulose, phthalicized gelatin, and the like), a synthesized high molecule (polymethacrylate, polyacrylate, polyalkyl methacrylate/acrylate copolymer, polystyrene/polymethacrylate copolymer, and the like), and the like. Among the above, the gelatin is preferable, and polyvinyl alcohol (PVA) or combining the gelatin with the polyvinyl alcohol (PVA) is more preferable. Examples of the gelatin include an inert gelatin (for example, Nitta gelatin 750), a phthalicized gelatin (for example, Nitta gelatin 801), and the like.

Preferable examples of the above polyvinyl alcohol (PVA) include the one described in JP-A No. 2000-171936 (paragraph No. 0009 to paragraph No. 0.020), specifically, a complete saponified matter PVA-105, a partly saponified matter PVA-205 and PVA-335, a modified polyvinyl alcohol MP-203 (made by KURARAY CO., LTD.), and the like.

The polyvinyl alcohol application amount (per support 1 $m^2$) of the above surface protective layer (per 1 layer) is preferably 0.3 g/$m^2$ to 4.0 g/$m^2$, and more preferably 0.3 g/$m^2$ to 2.0 g/$m^2$.

The above surface protective layer preferably contains an adhesion preventive. Examples of the adhesion preventive include wax, silica particle, styrene-contained elastomer block copolymer (for example, styrene-butadiene-styrene and styrene-isoprene-styrene), cellulose acetate, cellulose acetate butyrate, cellulose propionate, a mixture thereof, and the like. Moreover, the above surface protective layer may be added by i) a crosslinking agent, ii) a surfactant for improving applying property, and the like.

Especially, when the gas sensing material of the present invention is used for an application where the dimension change is at issue, using the polymer latex for the surface protective layer and the back layer is preferable. Description in terms of the above polymer latex is made in "Synthetic Resin Emulsion (edited by Taira Okuda and Hiroshi Inagaki, published by High Molecule Kankoukai (a company literally described as High Molecule Publication Association), 1978)," "Application of Synthesized Latex (edited by Takaaki Sugimura, Yasuo Kataoka, Souichi Suzuki, and Keiji Kasahara, published by High Molecule Kankoukai (a company literally described as High Molecule Publication Association), (1993))," "Chemistry of Synthesized Latex (written by Souichi Muroi, published by High Molecule Kankoukai (a company literally described as High Molecule Publication Association), (1970))," and the like.

Specific examples of the polymer latex include methyl methacrylate (33.5% by mass)/ethyl acrylate (50% by mass)/methacrylic acid (16.5% by mass) copolymer latex, methyl methacrylate (47.5% by mass)/butadiene (47.5% by mass)/itaconic acid (5% by mass) copolymer latex, ethyl acrylate (50% by mass)/methacrylic acid (50% by mass) copolymer latex, methyl methacrylate (58.9% by mass)/2-ethyl hexyl acrylate (25.4% by mass)/styrene (8.6% by mass)/2-hydroxy ethyl methacrylate (5.1% by mass)/acrylic acid (2.0% by mass) copolymer latex, methyl methacrylate (64.0% by mass)/styrene (9.0% by mass)/butyl acrylate (20.0% by mass)/2-hydroxy ethyl methacrylate (5.0% by mass)/acrylic acid (2.0% by mass) copolymer latex, and the like.

Moreover, examples of the binder for the surface protective layer include the combination of the polymer latexes described in JP-A No. 2000-267226, and the technology described in JP-A No. 2000-019678.

Ratio of the polymer latex of the above surface protective layer is preferably 10% by mass to 90% by mass relative to an entire binder, and more preferably 20% by mass to 80% by mass. The application amount (per support 1 $m^2$) of the entire binder (containing water-soluble polymer and latex polymer) of the above surface protective layer (per 1 layer) is preferably 0.3 $g/m^2$ to 5.0 $g/m^2$, and more preferably 0.3 $g/m^2$ to 2.0 $g/m^2$.

The preparation temperature of the gas sensing material according to the second embodiment is preferably 30° C. to 65° C., more preferably 35° C. to 60° C., and especially preferably 35° C. to 55° C.

Moreover, the temperature of the gas sensing material application liquid immediately after the adding of the polymer latex is preferably kept at 30° C. to 65° C. For improving silver color tone and the image's elapsed time change, the above back layer may be added by a coloring agent having an absorption maximum 300 nm to 450 nm. Examples of the coloring agent are described in JP-A No. 62-210458, JP-A No. 63-104046, JP-A No. 63-103235, JP-A No. 63-208846, JP-A No. 63-306436, JP-A No. 63-314535, JP-A No. 01-61745, JP-A No. 2001-100363, and the like.

The above coloring agent is, ordinarily, added preferably in a range of 0.1 $g/m^2$ to 1 $g/m^2$.

Adhesive Layer

The above adhesive layer may be formed on any of a first side to be provided with the above gas sensing layer and a second side free from the gas sensing layer. In view of sensitivity, however, setting the above adhesive layer on the first side to be provided with the gas sensing layer is preferable.

The above adhesive layer is not specifically limited, and therefore may be formed in any methods, preferably however, the adhesive layer and the peeling agent layer are sandwiched between the above support and the peeling support. In this case, the above adhesive layer is to be set on the gas sensing material sheet's side, and a set face may be located on any of a gas sensing material application face and a backface. For measurement, from an adhesive layer-adhered gas sensing material, a peeling support (to which a peeling agent layer is applied) is to be peeled off, then the gas sensing material sheet is to be sealably attached to the inspection object via the adhesive layer. After the measurement, the gas sensing material sheet is to be peeled off from a base body, to thereby carry out a heat development. When the adhesive layer causes inconvenience to the developing treatment, the thus peeled adhesive layer-adhered sheet may be once again attached to another support, followed by the heat development.

As the peeling support (to which the peeling agent is applied), a commercial product may be used. Depending on the object, the peeling support may be formed by applying the peeling agent on to the support. The peeling agent has a dynamic friction coefficient preferably in a range of 0.20 to 0.50, and those known in the art may be used as the peeling agent, examples thereof including silicon resin, fluorine resin, higher fatty acid, soap, wax, animal-plant oil, and the like. A silicon resin known in the releasing sheet industry may also be used, examples of the above peeling agent including: i) SD-7239, BY24-162, LTC-300B, LTC-350A, BY14-403, BY14-405, BY14-407, BY14-413, BY14-414, BY-14-411, and BY14-420 made by Dow Corning Toray Silicone Co., Ltd.; ii) KS-845, KS-770, KNS-202A, KNS-305, KNS-316, KNS-319, KNS-320, X-62-1232, and X-62-1233 made by Shin-Etsu Chemical Co., Ltd.; and the like.

Herein, application amount of the above peeling agent is preferably 0.4 $g/m^2$ to 2.0 $g/m^2$, and more preferably 0.6 $g/m^2$ to 1.3 $g/m^2$.

The above adhesive is not specifically limited, and therefore may be properly selected according to the object from those known in the adhesive industry, examples thereof including ethylene-vinyl acetate resin, acrylic emulsion resin, vinyl chloride resin, vinylidene chloride resin, synthetic rubber resin, natural rubber resin, and the like.

The above adhesive may be selected from those commercially available, examples thereof including: i) BPS-3233D, BPS-8170, BPS-3841, BPS-5215, BPS-1109, BPS-4849, and BPS-5569K made by Toyo Ink Mfg. Co., Ltd.; ii) SK-1717, SK-1233, SK-1435, SK-1473H, and SK-1633H made by Soken Chemical & Engineering Co., Ltd.; iii) Corponeel 2233, Corponeel 3816, and Corponeel 5859B, made by Nippon Synthetic Chemical Industry Co., Ltd.; and the like. Moreover, the acrylic latexes described in JP-A No. 4-298586 and JP-A No. 3-6277 may be used.

Examples of the above adhesive include solvent adhesive, emulsion adhesive, hot melt adhesive, and the like. Examples of the application apparatus include a comma coater, a reverse roll coater, an air knife coater, a knife coater, a die coater, and the like.

The application amount of the application liquid for the adhesive layer is preferably 5 $g/m^2$ to 40 $g/m^2$, and especially preferably, in view of i) easiness of tailoring and ii) an after-use stability of adhesion force, 10 $g/m^2$ to 30 $g/m^2$.

The above adhesive may be those having a high transparency and a proper adhesion force. It is necessary that the adhesive is not adhered to a chopping blade and the like in the applying operation, and that the adhesive has a sufficient adhesion force for adhering to the inspection object in the measurement. In response to the above requirement, the adhesive layer applied to the support (for example, polyester film) has an adhesion force to a flat stainless plate having a surface thereof cleaned with a degrease solvent such as alcohol, specifically, the above adhesion force is 300 g/25 mm width to 2000 g/25 mm width pursuant to JIS Z1538, thus meeting the above requirement.

Herein, the adhesion force of the adhesive can be measured in the following manner: i) to a first face of a commercially-available polyethylene terephthalate (PET) film (thickness 100 µm) which is otherwise prepared, the adhesive is applied (application amount 15 g/m$^2$) and dried, ii) then, the commercially-available polyethylene terephthalate (PET) film (thickness 100 µm) is tailored into 25 mm×500 mm (application part 25 mm×250 mm), iii) under 23° C.-55% RH, the commercially-available polyethylene terephthalate (PET) film is adhered to an adhesive face of a flat stainless plate 25 mm×500 mm which is cleaned with an alcohol, iv) mating those free from the adhesive layers, v) attach the mating by applying a load 2 kgf with a roller by three repeated rollings for crimping, vi) elapsed time 24 hours, and vii) pursuant to JIS Z1538, under 23° C.-55% RH, fix the stainless plate's first end free from the adhesive by using a clamp of an Instron tension tester. On the other hand, the polyethylene terephthalate film's first end free from the adhesive application is to be hanged downward, a terminal end thereof is to be clamped with a lower clamp, then the polyethylene terephthalate film is to be tensionally peeled in 180° direction at a rate of 300 mm/minute by using the Instron tension tester, to thereby measure the load.

The above gas sensing layer, the above surface protective layer, the above back layer and the like may be added by a film hardener. Examples of the film hardener include those described in the methods at page 77 to page 87 of "THE THEORY OF THE PHOTOGRAPHIC PROCESS FOURTH EDITION" (Macmillan Publishing Co., Inc. 1977) written by T. H. James, where chromium alum, 2,4-dichloro-6-hydroxy-s-triazine sodium salt, N,N-ethylene bis(vinyl sulphon acetamide), and N,N-propylene bis(vinyl sulphon acetamide) are described as the film hardener. Moreover, page 78 of "THE THEORY OF THE PHOTOGRAPHIC PROCESS FOURTH EDITION" (published by Macmillan Publishing Co., Inc., 1977) written by T. H. James and the like describe a polyvalent metal ion as the film hardener. Moreover, U.S. Pat. No. 4,281,060, JP-A No. 6-208193 and the like describe polyisocyanates. U.S. Pat. No. 4,791,042 and the like describe epoxy compounds. JP-A No. 62-89048 and the like describe vinyl sulfone compounds.

The above film hardener is added as a solution. This solution is to be added into the surface protective layer application liquid in a period from 180 minutes before the application to on the eve of the application, preferably from 60 minutes before the application to 10 seconds before the application. The mixing method and the mix condition are not specifically limited as long as the present invention is sufficiently effected, and thereby may be properly selected according to the object. Specific examples of the mixing method include i) using a mixing tank which makes an average staying time (which is calculated from A) the additive's flow rate and B) liquid conveying rate to a coater) into a desired time, and ii) using a static mixer described in chapter 8 of "Liquid Mix Technology" (published by THE NIKKAN KOGYO SHIMBUN, LTD., 1989) written by N. Harnby, M. F. Edwards and A. W. Nienow, translated by Kohji Takahashi, and the like.

The gas sensing material according to the second embodiment of the present invention may contain a charge preventing layer, a conductive layer, an evaporative metal layer, moreover may contain, an ionic polymer described in U.S. Pat. Nos. 2,861,056 and 3,206,312, an insoluble inorganic salt described in U.S. Pat. No. 3,428,451, and the like.

The applying method of the gas sensing material according to the second embodiment of the present invention is not specifically limited, and therefore may be properly selected according to the object, examples thereof including various coating operations such as an extrusion coating, a slide coating, a curtain coating, a dip coating, a knife coating, a flow coating, and an extrusion coating using a hopper (which is described in U.S. Pat. No. 2,681,294), preferable examples thereof including an extrusion coating and a slide coating described at page 399 to page 536 of "LIQUID FILM COATING" (CHAPMAN & amp; published by HALL, 1997) written by Stephen F. Kistler, Petert M. Schweizer, and especially preferable examples including a slide coating.

The shape of the slide coater used for the above slide coating is described in FIG. 11b. 1 at page 427 of "LIQUID FILM COATING" (CHAPMAN & amp; published by HALL, 1997) written by Stephen F. Kistler, Petert M. Schweizer. Moreover, when so desired, the method capable of coating two or more layers simultaneously may be used, examples thereof are described at page 399 to page 536 of "LIQUID FILM COATING" (CHAPMAN & amp; published by HALL, 1997), the method described in U.S. Pat. No. 2,761,791, and the method described in Great Britain Patent No. 837,095.

The gas sensing material of the present invention preferably has a film face pH before the heat developing treatment in a range of 7.0 or less, more preferably 6.6 or less, and especially preferably 4 to 6.2. The lower limit of the above pH is not specifically limit, but about 3.

For regulating the above film face pH, an organic acid such as phthalic acid derivative, a nonvolatile acid such as sulfuric acid, and a volatile base such as ammonia may be preferably used, from the viewpoint of decreasing the film face pH. Especially, the ammonia is preferable for accomplishing a low film face pH, since the ammonia is volatile and is removable before the applying operation or the heat development. Moreover, combination of the nonvolatile base (such as sodium hydroxide, potassium hydroxide, lithium hydroxide and the like) and ammonia is preferably used. In terms of the above, a method of measuring the film face pH is described in JP-A No. 2000-284399 (paragraph No. 0123).

For suppressing performance fluctuation when stored live or for improving curl, winding habit and the like, the gas sensing material according to the second embodiment of the present invention is preferably wrapped by a wrapping material having one of an oxygen permeability and a moisture permeability whichever is lower.

The wrapping material having one of the oxygen permeability and the moisture permeability whichever is lower is described, for example, in JP-A No. 8-254793, JP-A No. 2000-206653, and the like. In addition, other than those described above, examples of the technologies for the gas sensing material of the present invention include those described in EP803764A1, EP883022A1, International Publication No. WO98/36322, JP-A No. 56-62648, JP-A No. 58-62644, JP-A No. 9-43766, JP-A No. 9-281637, JP-A No. 9-297367, JP-A No. 9-304869, JP-A No. 9-311405, JP-A No. 9-329865, JP-A No. 10-10669, JP-A No. 10-62899, JP-A No. 10-69023, JP-A No. 10-186568, JP-A No. 10-90823, JP-A No. 10-171063, JP-A No. 10-186565, JP-A No. 10-186567, JP-A No. 10-186569 to JP-A No. 10-186572, JP-A No.

10-197974, JP-A No. 10-197982, JP-A No. 10-197983, JP-A No. 10-197985 to JP-A No. 10-197987, JP-A No. 10-207001, JP-A No. 10-207004, JP-A No. 10-221807, JP-A No. 10-282601, JP-A No. 10-288823, JP-A No. 10-288824, JP-A No. 10-307365, JP-A No. 10-312038, JP-A No. 10-339934, JP-A No. 11-7100, JP-A No. 11-15105, JP-A No. 11-24200, JP-A No. 11-24201, JP-A No. 11-30832, JP-A No. 11-84574, JP-A No. 11-65021, JP-A No. 11-109547, JP-A No. 11-125880, JP-A No. 11-129629, JP-A No. 11-133536, JP-A No. 11-133537, JP-A No. 11-133538, JP-A No. 11-133539, JP-A No. 11-133542, JP-A No. 11-133543, JP-A No. 11-223898, JP-A No. 11-352627, JP-A No. 11-305377, JP-A No. 11-305378, JP-A No. 11-305384, JP-A No. 11-305380, JP-A No. 11-316435, JP-A No. 11-327076, JP-A No. 11-338096, JP-A No. 11-338098, JP-A No. 11-338099, JP-A No. 11-343420, JP-A No. 2000-187298, JP-A No. 2000-10229, JP-A No. 2000-47345, JP-A No. 2000-206642, JP-A No. 2000-98530, JP-A No. 2000-98531, JP-A No. 2000-112059, JP-A No. 2000-112060, JP-A No. 2000-112104, JP-A No. 2000-112064, JP-A No. 2000-171936, and the like.

(Gas Inspecting Method)

The gas inspecting method of the present invention includes an adhering operation and a heat developing operation, moreover includes when necessary, other operations.

Adhering Operation

The adhering operation adheres the gas sensing material of the present invention to the surface of the inspection object.

Preferably, a gel gas sensing material containing at least the nonphotosensitive organic silver salt is to be applied to the surface of the inspection object.

Preferably, the gas sensing material having the gas sensing layer (which contains at least the nonphotosensitive organic silver salt) and the adhesive layer which are located on the support in this order is to be attached to surface of the inspection object via the adhesive layer.

Of the present invention, the gas sensing material can be manufactured by mixing the organic silver salt water dispersion solution with the binder. In this case, mixing two or more organic silver salt water dispersion solutions with two or more binders is preferable.

Of the present invention, the following operations are allowed: i) applying the nonphotosensitive heat developing liquid directly to the inspection object, followed by drying the resultant, and still followed by peeling the resultant, to thereafter carry out the heat developing treatment, ii) applying the nonphotosensitive heat developing liquid on to the support to thereby prepare the sheet-shaped application matter, then sealably attaching the sheet-shaped application matter to the inspection base body for measurement, and then subjecting the sheet-shaped application matter to the heat developing treatment.

In the case of the above sheet-shaped application matter, the following inspecting method is more preferable: The sheet-shaped application matter having an adhesive layer is sealably adhered to the inspection object via the adhesive layer for the inspection. In the case of the sheet-shaped application matter, inspection time can be decreased and the inspecting operation is easy, eliminating the need of an expert skill. Moreover, the application amount of the nonphotosensitive heat developing liquid becoming constant can improve accuracy and reproducibility of the inspection. In the latter case, the organic silver salt may be used by a desired amount, as a silver amount, however, 0.1 g/m$^2$ to 5 g/m$^2$ is preferable, 1 g/m$^2$ to 3 g/m$^2$ is more preferable, and 1.2 g/m$^2$ to 2.5 g/m$^2$ is especially preferable. In the latter case, measuring the developing quantity of the organic silver salt may accomplish a quantitative measurement.

The inspection object of the above gas sensing material is preferably a structure of a metal material.

Preferably, the above metal material is at least one selected from the group consisting of iron steel, aluminum, titanium, copper, nickel, stainless steel, alloy thereof, and intermetallic compound.

Examples of the above structure include structural material, gas storing receptor, fuel cell, construction material, atomic power facility, piping, bolt-and-nut, vehicle, pump, valve, burner, ingot, rolling material, extruding material, reinforcing material, and the like.

Heat Developing Operation

The heat developing operation subjects the gas sensing material to the heat developing treatment.

The heat developing treatment is not specifically limited, and therefore may be properly selected according to the object. Ordinarily, the inspection base body is exposed, followed by increasing temperature of the gas sensing material to thereby carry out the development. The development temperature is preferably 80° C. to 250° C., more preferably 100° C. to 140° C., still more preferably 110° C. to 130° C., and especially preferably 115° C. to 130° C. The developing time is preferably 1 second to 60 seconds, more preferably 5 seconds to 30 seconds, and especially preferably 10 seconds to 20 seconds.

As the heat developing method, a plate heater method is preferable. The plate heater method in JP-A No. 11-133572 is preferable, which describes a heat developing apparatus where a gas sensing material formed with a developing core is caused to contact a heating unit by means of a heat developing portion to thereby obtain a visual image. The heating unit is a plate heater. A plurality of press rollers are opposedly arranged along a first face of the plate heater. The gas sensing material is caused to pass between the press roller and the plate heater, to thereby carry out the heat development.

Preferably, the plate heater is separated into two stages to six stages, with a head end portion thereof having a decreased temperature about 1° C. to about 10° C. The method like the above is also described in JP-A No. 54-30032, where the water content and the organic solvent in the gas sensing material can be removed out of the system. Moreover, shape change of the support of the gas sensing material can be suppressed, which change is attributable to a rapid heating of the gas sensing material.

With the gas inspecting method using the gas sensing material of the present invention, a monochrome image by a silver image can be formed, the silver image forming position can specify the hydrogen gas leak part, and the silver image density or the silver image forming amount can quantify the hydrogen gas quantity.

Hereinafter described are details of the present invention by examples. The present invention is, however, not limited to the examples.

MANUFACTURING EXAMPLE 1

<Preparation of Gas Sensing Material-1>

Preparation of PET Support

Terephthalic acid and ethylene glycol were used. According to an ordinary method, polyethylene terephthalate (PET) having inherent viscosity (IV)=0.66 (phenol/tetrachloroethane=6/4 (mass ratio) measured at 25° C.) was synthesized. The thus obtained PET was pelletized, followed by drying at 130° C. for 4 hours, followed by melting at 300° C., followed by extruding from a T-TYPE die for rapid quenching, and followed by thermal fixing, to thereby prepare a non-drawn film having thickness 25 μm.

The thus obtained non-drawn film was drawn at 110° C. longitudinally to 3.3 times length with rolls having different circumferential speeds, then, was drawn at 130° C. laterally to 4.5 times length with a tenter. Then, the resultant was thermally fixed at 240° C. for 20 seconds, to thereafter relieve laterally by 4% at 240° C. Then, the tenter's chuck portion was slit, followed by knurling of both ends, and followed by winding at 4 kgf/cm$^2$, to thereby prepare a roll having thickness 25 μm.

Both faces of the thus obtained 2-axis drawn polyethylene terephthalate (PET) support having thickness 25 μm were subjected to a treatment with a solid state corona treating machine 6 KVA model (made by Pillar) under a room temperature at 20 m/minute. The corona discharge treatment had treating frequency 9.6 kHz, and a gap clearance 1.6 mm between an electrode and a dielectric roll.

Herein, from the reading of current and voltage, it was found that the support was subjected to the corona discharge treatment 0.375 kV·A·minute/m$^2$.

Then, to a first face (gas sensing layer's side face) of the support subjected to the corona discharge treatment, an undercoat application liquid composed of Pesresin A-520 (30% by mass solution, made by Takamatsu Oil & Fat Co., Ltd.) 59 g, polyethylene glycol monononyl phenyl ether (average ethylene oxide number=8.5, 10% by mass solution) 5.4 g, polymer fine particle (MP-1000, made by Soken Chemical & Engineering Co., Ltd., average particle diameter 0.4 μm) 0.91 g, and distilled water 935 mL was applied with a wire bar such that the wet application amount was 6.6 ml/m$^2$ (per one face), followed by drying at 180° C. for 5 minutes, to thereby form a surface undercoat layer.

Then, to a backface of the PET support, a backface first layer application liquid composed of styrene-butadiene copolymer latex (solid content 40% by mass, styrene/butadiene mass ratio=68/32) 158 g, 2,4-dichloro-6-hydroxy-S-triazine sodium salt 8% by mass water solution 20 g, lauryl benzene sodium sulfonate 1% by mass water solution 10 mL, and distilled water 854 mL was applied with a wire bar such that the wet application amount was 5.7 ml/m$^2$, followed by drying at 180° C. for 5 minutes, to thereby form a backface first layer.

On to the thus obtained backface first layer, a backface second layer application liquid composed of SnO$_2$/SbO (9/1 (mass ratio), average particle diameter 0.038 μm, 17% by mass dispersed matter) 84 g, gelatin (10% by mass water solution) 89.2 g, Metolose TC-5 (2% by mass water solution, made by Shin-Etsu Chemical Co., Ltd.) 8.6 g, polymer fine particle (MP-1000, made by Soken Chemical & Engineering Co., Ltd., average particle diameter 0.4 μm) 0.01 g, dodecylbenzene sodium sulfonate 1% by mass water solution 10 mL, NaOH (1% by mass) 6 mL, PROXEL (made by ICI) 1 mL, and distilled water 805 mL was applied with a wire bar such that the wet application amount was 7.7 ml/m$^2$, followed by drying at 180° C. for 6 minutes, to thereby form a backface second layer.

With the operations, the PET support was prepared.

Preparation of Fatty Acid Silver (Organic Silver Salt) Dispersed Matter

Behenic acid (branded as Edenor C22-85R, made by Henckel) 87.6 kg, distilled water 423 L, 5 mol/L density of NaOH water solution 49.2 L, and tert-butanol 120 L were mixed, followed by stirring at 75° C. for 1 hour for reaction, to thereby prepare a sodium behenate solution.

On the other hand, a water solution 206.2 L (pH 4.0) containing silver nitrate 40.4 kg was prepared, and was kept at 10° C.

Then, a reaction receptor receiving therein distilled water 635 L and tert-butanol 30 L was kept at 30° C., with sufficient stirring, total amount of the above sodium behenate solution and total amount of the above silver nitrate water solution were added respectively for 93 minutes 15 second and 90 minutes at a constant flow rate. In the above operation, the silver nitrate water solution alone was added for 11 minutes after start. Then, adding of the sodium behenate solution was started. After the adding of the silver nitrate water solution was ended, the sodium behenate solution alone was added for 14 minutes 15 seconds.

Hereinabove, the temperature in the reaction receptor was 30° C., and the outer temperature was so controlled that the liquid temperature was constant. Moreover, the piping of the adding system of the sodium behenate solution was kept at a constant temperature by circulating warm water outside the double tube, with the liquid temperature of the outlet of the adding nozzle's head end adjusted to 75° C. Moreover, the piping of the adding system of the silver nitrate water solution was kept at a constant temperature by circulating cool water outside the double tube. The adding position of the sodium behenate solution and the adding position of the silver nitrate water solution were symmetrical with respect to a centered stirring shaft, with the heights thereof so regulated as to prevent contact with a reaction solution.

Then, after adding the sodium behenate solution, the resultant was stirred and left at rest at then-temperature (as is) for 20 minutes, followed by temperature increase to 35° C. for 30 minutes, to thereafter carry out maturing for 210 minutes. Immediately after the maturing, a centrifugal filter was used for filtering solid content, followed by water cleaning of the solid content until the filter water had conductivity 30 μS/cm, to thereby prepare a fatty acid silver salt. The solid content of the thus obtained fatty acid silver salt was not dried but was stored as a wet cake.

Evaluation of the thus obtained behenic acid silver particle with an electronic microscope projection showed a scale-shaped crystal having average of the side AA=0.14 μm, average of the side BB=0.4 μm, average of the side CC=0.6 μm, average aspect ratio 5.2, average sphericity equivalent diameter 0.52 μm, and coefficient of variation of sphericity equivalent diameter 15% (where the side AA, the side BB, and the side CC denote the same as those described above).

Then, to the wet cake equivalent to the thus obtained dry solid content 260 kg, polyvinyl alcohol (branded as PVA-217, made by KURARAY CO., LTD.) 19.3 kg and water were added such that an entire amount was 1,000 kg to thereafter make the resultant into a slurry using a dissolver vane, then, a pipe line mixer (model PM-10 made by MIZUHO Industrial CO., LTD) was used for a preliminary dispersion.

Then, a stock solution after the preliminary dispersion was subjected to three treatments by regulating pressure of a dispersing machine (branded as Microfluidizer M-610, made by Microfluidex-International-Corporation, using Z-type interaction chamber) to 1,260 kgf/cm$^2$. In the cooling operation, corrugated tube heat exchangers were respectively installed in fore and aft positions of the interaction chamber, and coolant temperature was regulated, to thereby set the dispersion temperature at 18° C.

After the above operations, the fatty acid silver dispersed matter was prepared.

Preparation of Reducing Agent Complex Dispersed Matter

To i) "reducing agent complex-1" (2,2'-methylene bis-(4-ethyl-6-tert-butyl phenol) and triphenyl phosphine oxide 1:1 complex) 10 kg expressed by the following formula, ii) triphenyl phosphine oxide 0.12 kg, and iii) modified polyvinyl alcohol (Poval MP203 made by KURARAY CO., LTD.) 10% by mass water solution 16 kg, water 7.2 kg was added, then the resultant was sufficiently mixed, to thereby prepare a slurry. The thus prepared slurry was conveyed with a diaphragm pump, and was dispersed for 4 hours 30 minutes by means of a lateral sand mill (UVM-2: made by Imex) loaded with zirconia beads having an average diameter 0.5 mm, then benzoisothiazorinone sodium salt 0.2 g and water were added, to thereby prepare the reducing agent having density 25% by mass. After the above operations, the reducing agent complex dispersed matter was prepared.

A reducing agent complex particle contained in the thus obtained reducing agent complex dispersed matter had a median diameter 0.46 μm and a maximum particle diameter 1.6 μm or less. The thus obtained reducing agent complex dispersed matter was filtered with a polypropylene filter having pore diameter 3.0 μm for removing foreign matters such as dust and the like, and was then housed.

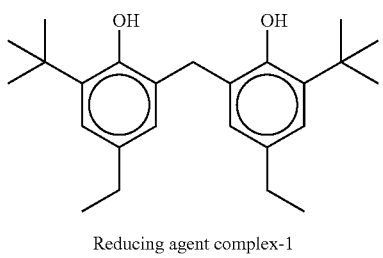

Reducing agent complex-1

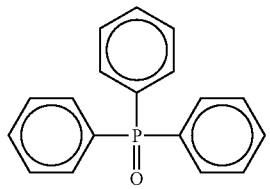

1:1 complex of the two

Preparation of Polyhalogen Compound-1 Dispersed Matter

To "polyhalogen compound-1" (tribromomethane sulfonyl benzene) 10 kg expressed by the following formula, modified polyvinyl alcohol (Poval MP203 made by KURARAY CO., LTD.) 20% by mass water solution 10 kg, triisopropyl naphthalene sodium sulfonate 20% by mass water solution 0.4 kg, water 14 kg was added, then the resultant was sufficiently mixed, to thereby prepare a slurry.

The thus prepared slurry was conveyed with a diaphragm pump, and was dispersed for 5 hours by means of a lateral sand mill (UVM-2: made by Imex) loaded with zirconia beads having an average diameter 0.5 mm, then benzoisothiazorinone sodium salt 0.2 g and water were added, to thereby prepare an organic polyhalogen compound having density 26% by mass. After the above operations, polyhalogen compound-1 dispersed matter was prepared.

An organic polyhalogen compound particle contained in the thus obtained polyhalogen compound-1 dispersed matter had a median diameter 0.41 μm and a maximum particle diameter 2.0 μm or less. The thus obtained organic polyhalogen compound dispersed matter was filtered with a polypropylene filter having pore diameter 10.0 μm for removing foreign matters such as dust and the like, and then was housed.

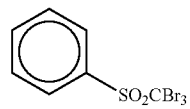

Polyhalogen compound-1

Preparation of Polyhalogen Compound-2 Dispersed Matter

To "polyhalogen compound-2" (N-butyl 3-tribromomethane sulfonyl benzamide) 10 kg expressed by the following formula, modified polyvinyl alcohol (Poval MP203 made by KURARAY CO., LTD.) 10% by mass water solution 20 kg, triisopropyl naphthalene sodium sulfonate 20% by mass water solution 0.4 kg, water 8 kg was added, then the resultant was sufficiently mixed, to thereby prepare a slurry. The thus prepared slurry was conveyed with a diaphragm pump, and was dispersed for 5 hours by means of a lateral sand mill (UVM-2, made by Imex) loaded with zirconia beads having an average diameter 0.5 mm, then benzoisothiazorinone sodium salt 0.2 g and water were added, to thereby prepare an organic polyhalogen compound having density 25% by mass. This dispersion solution was heated at 40° C. for 5 hours. After the above operations, polyhalogen compound-2 dispersed matter was prepared.

An organic polyhalogen compound particle contained in the thus obtained polyhalogen compound-2 dispersed matter had a median diameter 0.36 μm and a maximum particle diameter 1.5 μm or less. The thus obtained organic polyhalogen compound dispersed matter was filtered with a polypropylene filter having pore diameter 3.0 μm for removing foreign matters such as dust and the like, and then was housed.

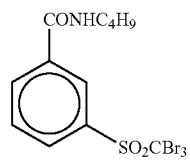

Polyhalogen compound-2

Preparation of Phthalazine Compound Solution

A modified polyvinyl alcohol MP203 (made by KURARAY CO., LTD.) 8 kg was dissolved in water 174.57 kg, then, triisopropyl naphthalene sodium sulfonate 20% by mass water solution 3.15 kg, and phthalazine compound-1 (6-isopropyl phthalazine) 70% by mass water solution 14.28 kg expressed by the following formula were added. After the above operations, phthalazine compound 5% by mass solution was prepared.

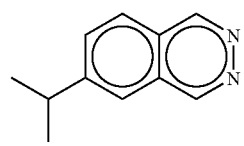

Phthalazine compound-1

Preparation of Mercapto Compound Water Solution

A "mercapto compound-1" (1-(3-sulfophenyl)-5-mercapto tetrasol sodium salt) 7 g expressed by the following formula was dissolved in water 993 g, to thereby prepare water solution of mercapto compound 0.7% by mass.

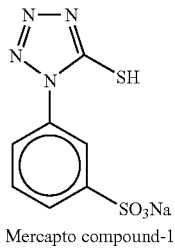
Mercapto compound-1

Preparation of SBR Latex Liquid

An ammonium persulfate as a polymerization starting agent, anion surfactant as an emulsifier, styrene 70.5 mass part, butadiene 26.5 mass part, and acrylic acid 3 mass part were subjected to an emulsification-polymerization, followed by aging at 80° C. for 8 hours. Then, the resultant was cooled to 40° C., and was caused to have pH 7.0 by ammonia water, then, Sandet BL (made by Sanyo Chemical Industries, Ltd.) was so added as to become 0.22%. Then, sodium hydroxide water solution 5% by mass was added to thereby bring about pH 8.3, then ammonia water was added to thereby adjust to pH 8.4. The mol ratio of $Na^+$ ion to $NH^{4+}$ ion used herein was 1:2.3. To this liquid 1 kg, benzoisothiazorinone sodium salt 7% by mass water solution 0.15 ml was added. After the above operations, the SBR latex liquid was prepared.

The thus obtained SBR latex had a glass transition temperature (Tg)=23° C., average particle diameter 0.1 μm, density 43% by mass, equilibrium water content 0.6% by mass at 25° C.-60% RH, ion conductivity 4.2 mS/cm (ion conductivity was measured with a conductivity meter CM-30S (made by Toa Denpa), with a latex stock solution (43% by mass) set at 25° C.).

Preparation of Gas Sensing Material Application Liquid-1

The fatty acid silver dispersed matter 1,000 g, water 104 ml, the polyhalogen compound-1 dispersed matter 6.3 g, the polyhalogen compound-2 dispersed matter 20.7 g, the phthalazine compound solution 173 g, SBR latex (Tg=23° C.) liquid 1,082 g, the reducing agent complex dispersed matter 258 g, and the mercapto compound solution 9 g were sequentially added, followed by a sufficient mixing. After the above operations, the gas sensing material application liquid-1 was prepared.

The thus obtained gas sensing material application liquid-1 (as is) was conveyed to a coating die for application.

Preparation of Intermediate Layer Application Liquid

To polyvinyl alcohol (PVA-205, made by KURARAY CO., LTD.) 10% by mass water solution 772 g and methyl methacrylate/styrene/butyl acrylate/hydroxy ethyl methacrylate/acrylic acid copolymer (copolymerization weight ratio 64/9/20/5/2) latex 27.5% by mass liquid 226 g, aerosol OT (made by American Cyanamid Co) 5% by mass water solution 2 ml and diammonium phthalate salt 20% by mass water solution 10.5 ml were added, then water was added to the resultant such that a total amount 880 g was obtained, and the pH was adjusted to 7.5 with NaOH. After the above operations, the intermediate layer application liquid was prepared.

The thus obtained intermediate layer application liquid was conveyed to a coating die in such a manner as to become 10 ml/m². The intermediate layer application liquid had viscosity 65 mPa·s measured with a B-type viscosimeter at 40° C. (No. 1 rotor, 60 rpm).

Preparation of Protective Layer First Layer Application Liquid

An inert gelatin 64 g was dissolved in water, then methyl methacrylate/styrene/butyl acrylate/hydroxy ethyl methacrylate/acrylic acid copolymer (copolymerization weight ratio 64/9/20/5/2) latex 27.5% by mass liquid 80 g, phthalic acid 10% by mass methanol solution 23 mL, 4-methyl phthalic acid 10% by mass water solution 23 mL, 0.5 mol/l density sulfuric acid 28 mL, aerosol OT (made by American Cyanamid Co) 5% by mass water solution 5 mL, phenoxy ethanol 0.5 g, and benzoisothiazorinone 0.1 g were added to the resultant, then water was added such that a total amount was 750 g, to thereby prepare an application liquid. On the eve of applying 4% by mass of chromium alum 26 ml to this application liquid, a protective layer first layer application liquid which is mixed by means of a static mixer was conveyed to a coating die in such a manner as to become 18.6 ml/m².

The thus obtained protective layer first layer application liquid had viscosity 20 mPa·s measured with a B-type viscosimeter at 40° C. (No. 1 rotor, 60 rpm).

Preparation of Protective Layer Second Layer Application Liquid

An inert gelatin 80 g was dissolved in water, then methyl methacrylate/styrene/butyl acrylate/hydroxy ethyl methacrylate/acrylic acid copolymer (copolymerization weight ratio 64/9/20/5/2) latex 27.5% by mass liquid 102 g, fluorine surfactant (N-perfluorooctyl sulfonyl-N-propyl alanine potassium salt expressed by the following formula F-1) 5% by mass solution 3.2 mL, fluorine surfactant (polyethylene glycol mono(N-perfluorooctyl sulfonyl-N-propyl 2-aminoethyl expressed by the following formula F-2) ether [ethylene oxide average polymerization=15]) 2% by mass water solution 32 mL, aerosol OT (made by American Cyanamid Co) 5% by mass solution 23 mL, polymethyl methacrylate fine particle (average particle diameter 0.7 μm) 4 g, polymethyl methacrylate fine particle (average particle diameter 4.5 μm) 21 g, 4-methyl phthalic acid 1.6 g, phthalic acid 4.8 g, sulfuric acid 44 ml having 0.5 mol/L density, and benzoisothiazorinone 10 ml were added by water such that a total amount 650 g was obtained. Then, on the eve of applying water solution 445 ml (containing 4% by mass of chromium alum and 0.67% by mass of phthalic acid), the resultant was mixed by means of a static mixer, to thereby prepare a protective layer second layer application liquid. The application liquid was so conveyed to a coating die as to become 8.3 ml/m².

The thus obtained application liquid had viscosity 19 mPa·s measured with a B-type viscosimeter at 40° C. (No. 1 rotor, 0 rpm).

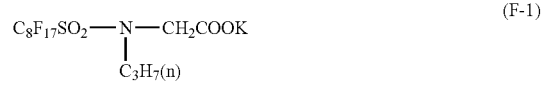

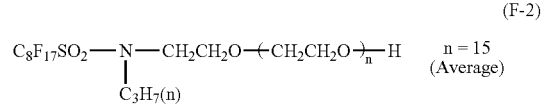

Preparation of "Gas Sensing Material Sheet-1"

To a backface of the above PET support, gelatin application amount 1.7 g/m² was applied, dried, to thereby form a back layer.

Then, on an opposite face of the above support's backface, from the undercoat face, the gas sensing layer, the intermediate layer, the protective layer first layer, the protective layer second layer were sequentially applied by a slide bead applying method (simultaneous overlapping layers).

Herein, in terms of temperature, the gas sensing layer and the intermediate layer were adjusted to 35° C., the protective layer first layer was adjusted to 36° C., and the protective layer second layer was adjusted to 37° C.

The above applying-drying conditions are as described below. The applying speed was 160 m/min, coating die head end and the support defined a gap therebetween 0.10 mm to 0.30 mm, a decompression chamber had a pressure which was 196 Pa to 882 Pa lower than an atmospheric pressure. Before application, the support was deelectrified by an ion wind. Subsequently, in a chilling zone, a wind having a dry bulb temperature 10° C. to 20° C. was used for cooling the application liquid, followed by a noncontact conveying, then a helical noncontact drying apparatus was used for drying with drying wind having a dry bulb temperature 23° C. to 45° C. and a wet bulb temperature 15° C. to 21° C. After the drying, humidity was adjusted at 25° C.-40 to 60% RH, then the film face was heated to 70° C. to 90° C. After the heating, the film face was cooled to 25° C.

After the above operations, the "gas sensing material sheet-1" was prepared.

Herein, The thus prepared "gas sensing material sheet-1" had the following application amount of the respective compounds of the gas sensing layer.

Behenic acid silver=6.19 g/m$^2$
Polyhalogen compound-1=0.04 g/m$^2$
Polyhalogen compound-2=0.12 g/m$^2$
Phthalazine compound-1=0.21 g/m$^2$
SBR latex=11.1 g/m$^2$
Reducing agent complex-1=1.54 g/m$^2$
Mercapto compound-1=0.002 g/m$^2$

MANUFACTURING EXAMPLE 2

Preparation of "Gas Sensing Material Sheet-2"

On to the polyethylene terephthalate transparent support, SD-7239 (made by Dow Corning Toray Silicone Co., Ltd.) was applied with a gravure coater in such a manner as to have dry mass 1.0 g/m$^2$, followed by drying and winding, and the a peel layer was provided, to thereby prepare a peeling support.

Then, on to the peel layer of the thus prepared peeling support, an adhesive (BPS-5569K made by Toyo Ink Mfg. Co., Ltd.) was applied with a comma coater in such a manner as to have a dry mass 20 g/m$^2$, followed by drying, to thereby form an adhesive layer.

Then, the application face of the above gas sensing material sheet-1 was attached to an adhesive layer application face of the above peeling support via a laminator, followed by winding. After the above operations, the "gas sensing material sheet-2" was prepared.

Alternatively, the following method may be adopted: i) applying the adhesive to the application face of the "gas sensing material sheet-2" to thereby form an adhesive layer, ii) then attaching via the peeling support and the laminator, and iii) winding.

The thus obtained "gas sensing material sheet-1" and "gas sensing material sheet-2" were cut into a proper size, then under an environment 25° C.-50% the resultant was wrapped with a wrapping material made of a polyethylene (50 μm) having a structure including PET (10 μm)/PE (12 μm)/aluminum foil (9 μm)/Ny (15 μm))/carbon 3% structure, followed by storage for two weeks at an ordinary temperature, to thereafter carry out the following evaluation.

Preparation of Inspection Object

The inspection object was prepared in the following manner. Specifically, a tubular hydrogen gas bomb storing a hydrogen gas 1 atm was prepared. Then, by using an Instron tension tester at a room temperature atmosphere, the gas bomb was given a tension deformation with a low strain speed in a range of $10^{-4}$ s$^{-1}$ to $10^{-7}$ s$^{-1}$. Likewise, five tubular hydrogen gas bombs having the same deformation were prepared. The surface of each of the tubular hydrogen gas bombs was preliminarily subjected to a dry polishing-buffing to have a mirror face.

COMPARATIVE EXAMPLE 1

Experiment by Hydrogen Microprint Technique (HMPT Method)

In a bright room, the following experiment was carried out. Specifically, a gel photographic atomic nucleus emulsion (L4 made by ILford) was melted with water at about 40° C., followed by diluting to 7 times at the same temperature with pure water, then a wire loop method was used for carrying out the application in such a manner as to cover a surface of the deformed part of the above hydrogen gas bomb. After leaving at rest for 24 hours, the bomb was dipped in the formaldehyde solution, to thereby harden the gelatin film. As a fixing treatment, the resultant was dipped in sodium thiosulfate water solution (15% by mass) for 3 minutes. After the fixing treatment, the surface was cleaned with pure water, followed by blower drying. Then, from the surface of the deformed part, 10 cm (square) emulsion film was peeled off, to thereby measure the number of developed silver particles through an optical microscopic (magnification 300) observation. From an optical microscopic image, it was verified that ultrafine arrays of reduced silver particles (although considerably discontinuous) were present along a slip line caused by the deformation.

COMPARATIVE EXAMPLE 2

Experiment by Hydrogen Microprint Technique (HMPT Method)

The comparative example 1 was likewise carried out, except that the bright room was replaced with a red safe light.

From the surface of the deformed part of the hydrogen gas bomb, 10 cm (square) emulsion film was peeled off, to thereby measure the number of developed silver particles through an optical microscopic (magnification 300) observation. From an optical microscopic image, it was verified that ultrafine arrays of reduced silver particles (although considerably discontinuous) were present along a slip line caused by the deformation.

EXAMPLE 1

Bright Room Experiment Using "Gas Sensing Material Application Liquid-1"

In a bright room, the following experiment was carried out. Specifically, a gel "gas sensing material application liquid-1" was kept at about 35° C., then a wire loop method was used for carrying out the application in such a manner as to cover a surface of a deformed part of the above hydrogen gas bomb. After leaving at rest for 24 hours, blower drying was carried out. Then, from the surface of the deformed part of the hydrogen gas bomb, 10 cm (square) coating film was peeled off, and was sealably attached for 15 seconds on to a plate heater heated at 120° C., to thereby carry out the heat developing treatment.

With the coating film after the heat developing treatment, the number of developed silver particles was measured through an optical microscopic (magnification 300) observation. From an optical microscopic image, it was verified that arrays of visible black reduced silver (developed silver) particles were present along a slip line caused by the deformation.

EXAMPLE 2

Bright Room Experiment Using "Gas Sensing Material Sheet-1"

In a bright room, the following experiment was carried out. Specifically, the above "gas sensing material sheet-1" tailored into 10 cm (square) was sealably attached in such a manner as to cover a surface of a deformed part of the above hydrogen gas bomb. After leaving at rest for 24 hours, the gas sensing material sheet was peeled off, and was sealably attached for 15 seconds on a plate heater heated at 120° C., to thereby carry out the heat developing treatment.

With the gas sensing material sheet after the heat developing treatment, the number of developed silver particles was measured through an optical microscopic (magnification 300) observation. From an optical microscopic image, it was verified that arrays of visible black reduced silver (developed silver) particles were present along a slip line caused by the deformation.

EXAMPLE 3

Dark Room Experiment Using "Gas Sensing Material Sheet-1"

The example 2 was likewise carried out, except that the bright room was replaced with a red safe light.

With the gas sensing material sheet after the heat developing treatment, the number of developed silver particles was measured through an optical microscopic (magnification 300) observation. From an optical microscopic image, it was verified that arrays of visible black reduced silver (developed silver) particles were present along a slip line caused by the deformation.

EXAMPLE 4

Bright Room Experiment Using "Gas Sensing Material Sheet-2"

The example 2 was likewise carried out, except that the above "gas sensing material sheet-1" was replaced with the above "gas sensing material sheet-2". Specifically, in a bright room, the peeling support was peeled from the "gas sensing material sheet-2", then the "gas sensing material sheet-2" was sealably attached on to a surface of the deformed part of the above hydrogen gas bomb via an adhesive in such a manner as to cover the surface of the deformed part of the above hydrogen gas bomb. After leaving at rest for 24 hours, the gas sensing material sheet was peel off, an otherwise prepared polyethylene terephthalate (PET) transparent support was attached to the gas sensing material sheet, to thereby prepare a measured sample. Then, this measured sample was sealably attached for 15 seconds to a plate heater heated at 120° C., to thereby carry out the heat developing treatment.

With the sample after the heat developing treatment, the number of developed silver particles was measured through an optical microscopic (magnification 300) observation. From an optical microscopic image, it was verified that arrays of visible black reduced silver (developed silver) particles were present along a slip line caused by the deformation.

EXAMPLE 5

Dark Room Experiment Using "Gas Sensing Material Sheet-2"

The example 3 was likewise carried out, except that the above "gas sensing material sheet-1" was replaced with the above "gas sensing material sheet-2". Specifically, under a red safe light, the peeling support was peeled from the "gas sensing material sheet-2", then the "gas sensing material sheet-2" was sealably attached on to a surface of the deformed part of the above hydrogen gas bomb via an adhesive in such a manner as to cover the surface of the deformed part of the above hydrogen gas bomb. After leaving at rest for 24 hours, the gas sensing material sheet was peeled off, an otherwise prepared polyethylene terephthalate (PET) transparent support was attached to the gas sensing material sheet, to thereby prepare a measured sample. Then, this measured sample was sealably attached for 15 seconds to a plate heater heated at 120° C., to thereby carry out the heat developing treatment.

With the sample after the heat developing treatment, the number of developed silver particles was measured through an optical microscopic (magnification 300) observation. From an optical microscopic image, it was verified that arrays of visible black reduced silver (developed silver) particles were present along a slip line caused by the deformation.

<Evaluation of Rapid Property of Experiment>

In terms of rapid property of the experiment of each of the comparative example 1 to the comparative example 2 and the example 1 to the example 5, an actual operation time was evaluated by deducing 24-hour left at rest time from a total experiment time. Results are shown in the following Table 1.

<Evaluation of the Number of Experiments Required for Expert Skill>

In terms of easiness of the experiment of each of the comparative example 1 to the comparative example 2 and the example 1 to the example 5, the number of experiments required for expert skill was evaluated. Results are shown in the following Table 1.

<Evaluation of Experiment Accuracy>

In terms of accuracy (reproducibility) of the experiment of each of the comparative example 1 to the comparative example 2 and the example 1 to the example 5, each experiment was repeated 100 times, to thereby obtain coefficient of variation CV (%) of the number of measured developed silver particles. Results are shown in the following Table 1.

TABLE 1

|  | Actual operation time | The number of experiments for expert skill | Coefficient of variation after 100 experiments |
|---|---|---|---|
| Comparative example 1 | 180 minutes | 15 | 43% |
| Comparative example 2 | 180 minutes | 30 | 33% |
| Example 1 | 90 minutes | 5 | 20% |
| Example 2 | 25 minutes | 3 | 15% |
| Example 3 | 23 minutes | 5 | 14% |
| Example 4 | 15 minutes | 1 | 11% |
| Example 5 | 15 minutes | 4 | 12% |

From the results in Table 1, the example 1 to the example 5 show no problem in repeatability and reproducibility with the bright room experiment, bringing about high accuracy. Moreover, in the example 1 to the example 5, a short time experiment is accomplished. Especially, in the example 2 to the example 5 using the gas sensing material sheet, an extremely short time experiment is accomplished. Moreover, being free from a complicated developing treatment, the example 1 to the example 5 does not require the expert skill for the experimental operation. Especially, the example 2 to the example 4 showing the experiment using the gas sensing material sheet in the bright room carries out a simple operation in a bright place, thereby hardly requiring the expert skill. Moreover, the example 4 to the example 5 using the "gas sensing material sheet-2" having the adhesive layer can increase measurement accuracy, thus carrying out the measuring operation easily and rapidly. Moreover, the example 4 to the example 5 having the developed silver (which is a measurement result) in a state of being interposed between the supports shows that the measurement result can be stored for a long time.

Contrary to the above, in the comparative example 1 to the comparative example 2 by the conventional hydrogen microprint technique (HMPT method), a long-term operation is necessary and complicated developing treatment is required, thereby requiring the expert skill. Especially, the experiment in the bright room shows a deteriorated reproducibility.

<Measurement of Density>

With the samples obtained through the experiment of each of the comparative example 1 to the comparative example 2 and the example 1 to the example 5, a scanning measurement (aperture: diameter 1 mm) was carried out using a micro densitometer in a direction perpendicular to the slide line part caused by the deformation. The number of scannings was 10, calculating an average of the maximum density (ODmax).

Simultaneously with the above, a Macbeth densitometer RD910 (aperture: diameter 3 mm) was used for measuring the visible density (OD) of the deformed part.

Results are shown in the following Table 2.

TABLE 2

| | Micro densitometer measurement | | Macbeth densitometer measurement | |
|---|---|---|---|---|
| | Average ODmax | Coefficient of variation | Average ODmax | Coefficient of variation |
| Comparative example 1 | ≦0.01 | Not measurable | ≦0.01 | Not measurable |
| Comparative example 2 | ≦0.01 | Not measurable | ≦0.01 | Not measurable |
| Example 1 | 0.26 | 9% | 0.14 | 8% |
| Example 2 | 0.25 | 7% | 0.13 | 5% |
| Example 3 | 0.23 | 6% | 0.13 | 5% |
| Example 4 | 0.24 | 5% | 0.12 | 3% |
| Example 5 | 0.23 | 5% | 0.12 | 3% |

From the results in Table 2, the comparative example 1 and the comparative example 2 cannot measure the density with the micro densitometer (ordinarily used) and the Macbeth densitometer (easy measurement).

Contrary to the above, the example 1 to the example 5 can measure the density with both the micro densitometer (ordinarily used) and the Macbeth densitometer (easy measurement), accomplishing an easier and more rapid measurement. In addition, the result (of the coefficient of variation of the example 1 to the example 5) smaller than the result (of the coefficient of variation by the method of calculating the number of silver particle in Table 1) shows that combining with the density measurement can bring about a gas sensing sheet that is excellent in reproducibility and quantitative property.

The gas sensing material of the present invention may be preferably used for sensing the hydrogen gas and the sulfur-contained gas which are leaked or ejected from the surface of various inspection objects.

Moreover, the gas inspecting method of the present invention can easily and rapidly inspect the gas leak or gas ejection from the structural material, gas storing receptor, construction material, atomic power facility, piping, bolt-and-nut, vehicle, pump, valve, burner, ingot, rolling material, extruding material, reinforcing material, and the like each of which is made of the metal material selected from the group consisting of iron steel, aluminum, titanium, copper, nickel, stainless steel, alloy thereof, and intermetallic compound.

What is claimed is:

1. A gas inspecting method, comprising steps as follows in this order:
    adhering a gas sensing material to a surface of an inspection object/ wherein the gas sensing material comprises (i) a nonphotosensitive organic silver salt and (ii) at least one of a heat developer and a binder;
    exposing the gas sensing material to a potential source of the gas;
    thereafter heat developing the gas sensing material; and
    evaluating the number of developed silver particles on the developed gas sensing material to determine if gas had contacted the gas sensing material.

2. The gas inspecting method according to claim 1, wherein the gas sensing material which is in a form of a gel is applied to the surface of the inspection object.

3. The gas inspecting method according to claim 1, wherein the heat developing is carried out at 80° C. to 250° C. for 1 second to 60 seconds.

4. The gas inspecting method according to claim 1, wherein the inspection object has a structure made of a metal material.

5. The gas inspecting method according to claim 1, wherein the metal material is at least one selected from the group consisting of icon steel, aluminum, titanium, copper, nickel, stainless steel, alloy thereof, and intermetallic compound.

6. The gas inspecting method according to claim 1, wherein the structure is at least one selected from the group consisting of a structural material, a gas storing receptor, a construction material, an atomic power facility, a fuel cell, a piping, a bolt-and-nut, a vehicle, a pump, a valve, a burner, an ingot, a rolling material, an extruding material and a reinforcing material.

7. A gas inspecting method, comprising steps as follows in this order:
    adhering a gas sensing material to a surface of an inspection object, wherein the gas sensing material comprises:
    a support, and
    a gas sensing layer which comprises (i) a nonphotosensitive organic silver salt and (ii) at least one of a heat developer and a binder;
    exposing the gas sensing material to a potential source of the gas;
    thereafter heat developing the gas sensing material; and
    evaluating the number of developed silver particles on the developed gas sensing material to determine if gas had contacted the gas sensing material.

8. The gas inspecting method according to claim 7, wherein the gas sensing material is attached to the surface of the inspection object via an adhesive layer.

9. The gas inspecting method according to claim 7, wherein the heat developing is carried out at 80° C. to 250° C. for 1 second to 60 seconds.

10. The gas inspecting method according to claim 7, wherein the inspection object has a structure made of a metal material.

11. The gas inspecting method according to claim 7, wherein the metal material is at least one selected from the group consisting of iron steel, aluminum, titanium, copper, nickel, stainless steel, alloy thereof, and intermetallic compound.

12. The gas inspecting method according to claim 7, wherein the structure is at least one selected from the group consisting of a structural material, a gas storing receptor, a construction material, an atomic power facility, a fuel cell, a piping, a bolt-and-nut, a vehicle, a pump, a valve, a burner, an ingot, a rolling material, an extruding material and a reinforcing material.

13. The gas inspecting method according to claim 1, wherein the gas sensing material which comprises the nonphotoconductive organic silver salt is silver salt of a long-chain aliphatic carboxylic acid which comprises 10 to 30 carbon atoms, is applied to the surface of the inspection object.

14. The gas inspecting method according to claim 1, wherein the gas sensing material which comprises the nonphotoconductive organic silver salt is scale-shaped.

15. The gas inspecting method according to claim 14, wherein the scale-shaped nonphotoconductive organic silver salt has an X which is calculated from the following mathematical expression 1 and has an average 1.5 or more:

$$X=BB/AA; \quad \text{Mathematical expression 1}$$

wherein a shape of an organic silver salt particle is approximated into a rectangular parallelopiped, and wherein, in the mathematical expression 1, of a side AA, a side BB, and a side CC of the rectangular parallelopiped, the side AA is the shortest and the side BB is the second shortest, with the side CC and the side BB adapted to have a same length.

16. The gas inspecting method according to claim 1, wherein the gas sensing material which comprises the nonphotoconductive organic silver salt has a content as a silver amount in a range of 0.1 g/m² to 5 g/m², is applied to the surface of the inspection object.

17. The gas inspecting method according to claim 1, wherein the gas sensing material which comprises the heat developer is at least one selected from the group consisting of a hindered phenols reducing agent arid a bisphenols reducing agent, is applied to the surface of the inspection object.

18. The gas inspecting method according to claim 1, wherein the gas sensing material is adhered to an inspection object, to thereby sense a gas which is at least one of being leaked and being ejected from the inspection object.

19. The gas inspecting method according to claim 18, wherein the gas is one of a hydrogen gas and a sulfur-contained gas.

20. The gas inspecting method according to claim 7, wherein the gas sensing material which comprises the nonphotoconductive organic silver salt is silver salt of a long-chain aliphatic carboxylic acid which comprises 10 to 30 carbon atoms, is attached to the surface of the inspection object via the adhesive layer.

21. The gas inspecting method according to claim 7, wherein the gas sensing material which comprises the nonphotoconductive organic silver salt is scale-shaped, is attached to the, surface of the inspection object via the adhesive layer.

22. The gas inspecting method according to claim 21, wherein the scale-shaped nonphotoconductive organic silver salt has an X which is calculated from the following mathematical expression 1 and has an average 1.5 or more:

$$X=BB/AA; \quad \text{Mathematical expression 1}$$

wherein a shape of an organic silver salt particle is approximated into a rectangular parallelopiped, and wherein, in the mathematical expression 1, of a side AA, a side BB, and a side CC of the rectangular parallelopiped, the side AA is the shortest and the side BB is the second shortest with the side CC and the side BB adapted to have a same length.

23. The gas inspecting method according to claim 7, wherein the gas sensing material which comprises the nonphotoconductive organic silver salt has a content as a silver amount in a range of 0.1 g/m² to 5 g/m², is attached to the surface of the inspection object via the adhesive layer.

24. The gas inspecting method according to claim 7, wherein the gas sensing material which comprises the heat developer is at least one selected from the group consisting of a hindered phenols reducing agent and a bisphenols reducing agent, is attached to the surface of the inspection object via the adhesive layer.

25. The gas inspecting method according to claim 7, wherein the gas sensing material is adhered to an inspection object to thereby sense a gas which is at least one of being leaked and being ejected from the inspection object.

26. The gas inspecting method according to claim 25, wherein the gas is one of a hydrogen gas and a sulfur-contained gas.

* * * * *